(12) United States Patent
Jiang et al.

(10) Patent No.: US 11,197,914 B2
(45) Date of Patent: *Dec. 14, 2021

(54) GLP-1R/GCGR DUAL TARGET AGONIST POLYPEPTIDE FOR TREATMENT OF FATTY LIVER DISEASES, HYPERLIPEMIA AND ARTERIOSCLEROSIS

(71) Applicant: Shenzhen Turier Biotech Co., Ltd., Shenzhen (CN)

(72) Inventors: Xianxing Jiang, Guangzhou (CN); Rui Wang, Guangzhou (CN)

(73) Assignee: Shenzhen Turier Biotech Co. Ltd.

( * ) Notice: Subject to any disclaimer, the term of this patent is extended or adjusted under 35 U.S.C. 154(b) by 26 days.

This patent is subject to a terminal disclaimer.

(21) Appl. No.: 16/089,228

(22) PCT Filed: May 11, 2016

(86) PCT No.: PCT/CN2016/081741
§ 371 (c)(1),
(2) Date: Sep. 27, 2018

(87) PCT Pub. No.: WO2017/181452
PCT Pub. Date: Oct. 26, 2017

(65) Prior Publication Data
US 2019/0117737 A1    Apr. 25, 2019

(30) Foreign Application Priority Data

Apr. 22, 2016    (CN) .......................... 201610255395.9

(51) Int. Cl.
| | | |
|---|---|---|
| *A61K 38/22* | (2006.01) | |
| *C07K 14/575* | (2006.01) | |
| *A61P 3/08* | (2006.01) | |
| *A61P 1/16* | (2006.01) | |
| *A61P 3/06* | (2006.01) | |

(52) U.S. Cl.
CPC ............... *A61K 38/22* (2013.01); *A61P 1/16* (2018.01); *A61P 3/06* (2018.01); *A61P 3/08* (2018.01); *C07K 14/575* (2013.01)

(58) Field of Classification Search
CPC .............................. A61K 38/22; C07K 14/575
See application file for complete search history.

(56) References Cited

U.S. PATENT DOCUMENTS 10,479,819 B2 * 11/2019 Jiang ................... C07K 14/605
2017/0183383 A1 * 6/2017 Jiang ................... C07K 14/605

FOREIGN PATENT DOCUMENTS

| CN | 104507492 A | 4/2015 |
|---|---|---|
| CN | 104926934 A | 9/2015 |
| GN | 101389648 A | 3/2009 |
| JP | 2015524427 A5 | 3/2017 |
| WO | 2011/143209 A1 | 11/2011 |
| WO | 2015/095406 A1 | 6/2015 |
| WO | 2016/045400 A1 | 3/2016 |
| WO | WO2016043533 A1 | 3/2016 |

OTHER PUBLICATIONS

Willebrords et al., 2015, Strategies, models and biomarkers in experimental non-alcoholic fatty liver disease research, Pro Lipid Res , 59: 106-125.*
Office Action dated Feb. 12, 2020 in Japanese Application No. 2018-555579.
Search Report dated Jan. 17, 2019 in CN patent application No. 201610255395.9.
Pocai et al. "Glucagon-Like Peptide 1/Glucagon Receptor Dual Agonism Reverses Obesity in Mice", Diabetes, vol. 58, Oct. 2009, pp. 2258-2266.
Sun, "Progress in research on fatty liver fibrosis", Journal of Integrated Traditional and Western Medicine on Liver Diseases, vol. 13 No. 2, 2003.
European Search Report dated Nov. 28, 2019 in EU 16899039.8.
Alessia Santoprete et al.: "DPP-IV-resistant, long-acting oxyntomodulin derivatives", Journal of Peptide Science, vol. 17, No. 4, Apr. 1, 2011 (Apr. 1, 2011), pp. 270-280, XP055000397, ISSN: 1075-2617, DOI: 10.1002/osc.1328.
S Jung et al.: "Potent weight loss mechanism and improvement of NASH by the long-acting GLP-1/glucagon Yeceptor dual agonist HM12525A", Abstracts of 51st EASD Annual Meeting, vol. 58, Sep. 1, 2015 (Sep. 1, 2015), pp. S380-S381, XP055611969, DOI: 10.1007/s00125-015-3687-4.
International Search Report dated Jan. 23, 2017, in related PCT Application No. PCT/CN2016/081741.
Armstrong MJ, Gaunt P, Aithal GP, et al., "Liraglutide safety and efficacy in patients with non-alcoholic steatohepatitis (LEAN): a multicentre, double-blind, randomised, placebo-controlled phase 2 study", Lancet, 2015. Joi: 10.1016/S0140-6736( 15)00803-X.
Trevaskis JL, Griffin PS, Carrie W, et al. "Glucagon-like peptide-1 receptor agonism improves metabolic, biochemical, and histopathological indices of nonalcoholic steatohepatitis in mice", AJP Gastrointestinal & Liver Physiology, 2012, 302(8):G762-72.
Campbell JE, Drucher DJ, "Islet a cells and glucagon—critical regulators of energy homeostasis", Nature Reviews Endocrinology, 2015, 11(6):329-338.
Bendele A, Seely J, Richey C, et al., "Short Communication: Renal Tubular Vacuolation in Animals Treated with Polyethylene-Glycol-Conjugated Proteins", Toxicological Sciences, 1998,42(2): 152-157.

* cited by examiner

*Primary Examiner* — Amber D Steele
(74) *Attorney, Agent, or Firm* — Maschoff Brennan; Jonathan M. Benns

(57) ABSTRACT

The invention relates to uses of polypeptide compounds having dual target agonist effect on glucagon-like peptide-1 receptor (GLP-1R) and glucagon receptor (GCGR). Characterized by high enzymolysis stability, high biological activity and no adverse reaction, the polypeptide compounds are capable of reducing abnormal increase of triglycerides and total cholesterol in blood induced by diabetes mellitus and high fat diet, reducing liver enzyme level, reducing liver injury and fibrosis stage, and preventing or treating non-alcoholic fatty liver diseases (NAFLDs), hyperlipemia and arteriosclerosis.

9 Claims, 8 Drawing Sheets

Specification includes a Sequence Listing.

GLP-1R/GCGR DUAL TARGET AGONIST POLYPEPTIDE FOR TREATMENT OF FATTY LIVER DISEASES, HYPERLIPEMIA AND ARTERIOSCLEROSIS

CROSS-REFERENCE

This patent application is a nationalization of International PCT Application No. PCT/CN2016/081741 filed on May 11, 2016, which claims priority to Chinese Application No. 201610255395.9 filed on Apr. 22, 2016, which applications are incorporated herein by specific reference in their entirety.

FIELD OF THE INVENTION

The present invention belongs to the field of biochemical technology, and specially relates to a GLP-1R/GCGR dual target agonist polypeptide. The present invention also relates to preventive and/or therapeutic uses of the dual target agonist polypeptide for non-alcoholic fatty liver diseases, hyperlipemia and arteriosclerosis.

BACKGROUND OF THE INVENTION

Non-alcoholic fatty liver disease (NAFLD) is a progressive complex liver disease caused by non-excessive consumption of alcohol: NAFLD starts from fatty degeneration, non-alcoholic steatohepatitis (NASH), and further develops into hepatic fibrosis and cirrhosis, and eventually develops into hepatocellular carcinoma or hepatic failure. The global prevalence of NAFLD has doubled in the past three decades, and the number of the patients with NAFLD in China has reached 270 million. There is no correlation between single fatty degeneration and increasing short-term morbidity or mortality, but the risks of hepatic cirrhosis, hepatic failure and hepatocellular carcinoma for the patients with NASH significantly increase. NASH-induced hepatic cirrhosis is one of the main reasons for liver transplantation. In addition, the morbidity and mortality of cardiovascular diseases caused by liver diseases are significantly higher for patients with NASH than the normal population. The growing morbidity of NAFLD is bound to result in further shortage and consumption of limited medical resources.

NASH is widely considered to be a hepatic manifestation of such metabolic syndromes as type II diabetes, insulin resistance, central obesity, hyperlipemia and hypertension. Disorder of glucolipide metabolism can cause diabetes, NASH, atherosclerosis and other diseases. The NASH will further aggravate the diabetes and atherosclerosis-related vascular complications, and eventually cause organ fibrosis and organ failure.

Effective drugs for treating NAFLD/NASH is still not available now. The long-time safety and therapeutic effectiveness of such novel drugs under research as PPAR-γ insulin-like sensitizers, obeticholic acid and other farnesoid X receptor (FXR) agonists require to be further proved (Armstrong M J, Gaunt P, Aithal G P, et al. Lancet, 2015. doi:10.1016/50140-6736(15)00803-X.). The polypeptide drugs have the following advantages: first, most of them are derived from endogenous peptides or other natural peptides, and have clear structures and mechanisms of action; second, compared with general small-molecule drugs, they have higher activity, less dosage, less toxic side effects, with amino acids as the end product of metabolism (free of toxic side effects); third, compared with the foreign proteins, they have low immunogenicity, and can be chemically synthesized, and the product has high purity and controllability on quality; and fourth, polypeptide drugs are often able to avoid the gastrointestinal digestion and overcome the drawbacks that protein molecules are destroyed by digestive enzymes and thus cannot be orally administrated.

Glucagon-like peptide-1 (GLP-1) is a glucose-dependent incretin. Human GLP-1 is derived from proglucagon. Proglucagon consists of 158 amino acids and cleaved into different peptide chains at different sites. The GLP-1 is combined with the GLP-1 receptor in islet β-cell to activate the cyclic adenosine monophosphate (cAMP) pathway and mitogen-activated protein kinase (MAPK) pathway in cell membrane, and stimulate the synthesis and secretion of insulin with glucose. In addition, GLP-1 also has pharmacological functions to protect and promote the islet β-cell proliferation, improve insulin sensitivity, inhibit glucagon secretion, inhibit gastric emptying, reduce appetite, inhibit food intake and control body weight. Because the natural human GLP-1 has a very short half-life and lacks druggability, the structure of the natural GLP-1 is need to be optimized and modified to prolong the biological half-life of such drugs. These GLP-1 derivatives are structurally and functionally similar to GLP-1, and they can be combined with GLP-1R to activate the GLP-1R. Thus these derivatives are referred to as GLP-1 analogues or GLP-1R agonists. In the rodent model of NASH, the GLP-1 analogues can decrease liver enzyme level and oxidative stress, ameliorate liver lipid metabolism disorders, inhibit lipid oxidation, and reduce histological injury of liver (Trevaskis J L, Griffin P S, Carrie W, et al. *Ajp Gastrointestinal & Liver Physiology,* 2012, 302(8):G762-72.). Liraglutide is a long-lasting GLP-1 analogue, and is able to significantly improve the clinical signs of patients with NAFLD and NASH, significantly reduce the body weight of obese patients and improve pathoglycemia. (Armstrong M J, Gaunt P, Aithal G P, et al. *Lancet,* 2015. doi:10.1016/50140-6736(15)00803-X.).

However, up to now, the pharmacokinetics and safety of the GLP-1 analogues are not clear, and it is unclear how the introduced foreign chemical groups are metabolized and excreted and how do they influence human body, and thus further investigation is needed.

Glucagon is a hormone secreted by islet α-cell, which is composed of a single-chain polypeptide consisting of 29 amino acids. Glucagon is specifically bond to the glucagon receptor (GCGR) on the surface of the target cells of liver and kidney to activate endocellular adenylate cyclase, raise endocellular cAMP level and play physiological functions. Glucagon is a hormone stimulating catabolism. Short-term injection of glucagon can promote glycogenolysis and gluconeogenesis, and cause a rise in blood sugar. Glucagon and insulin are a pair of hormones with opposite functions that form a negative feedback control loop to maintain glucose homeostasis. Even more importantly, the results of animal and human trials show that long-term activation of GCGR by injection of glucagon can decrease appetite, stimulate fatty acid decomposition, and significantly increase energy consumption of adipose tissue (Campbell J E, Drucker D J. *Nature Reviews Endocrinology,* 2015, 11(6):329-338.).

The most common means of improving the in vivo half-life of polypeptides and reducing the frequency of polypeptide administration is to conjugate to mono-methoxy polyethylene glycol (methoxypolyethylene glycol, mPEG), by increasing the polypeptide molecular exclusion volume, reducing renal filtration clearance rate of the drug molecule, thereby prolonging the mPEG-modified drug's plasma half-life, so as to achieve the goal of reducing the administration frequency. However, the biological activities of most of the proteins are decreased with different degrees by this method. Even more dangerous is, mPEG is a molecule that cannot be metabolized in human body, the polypeptide protein drugs derived from it may lead to renal vacuolation (Bendele A, Seely J, Richey C, et al. *Toxicological Sciences*, 1998, 42(2):152-157.). The toxicity of mPEG is often overlooked greatly. Therefore, it is necessary to develop safe and effective polypeptide drugs for the clinical treatment of non-alcoholic fatty liver diseases and other chronic diseases requiring long-term medication.

SUMMARY OF THE INVENTION

In the Chinese patent application No. 201510237027.7, by molecule modification of oxyntomudulin (OXM) the inventor has obtained a kind of GLP-1R/GCGR dual target agonists as oxyntomudulin analogues having a longer half-life and insulinotropic activity without adverse events. The GLP-1R/GCGR dual target agonists can be used for treatment of diseases such as diabetes. Further experiments are carried out for the present invention, and new biological activity of such GLP-1R/GCGR dual target agonist polypeptides and their therapeutic uses and indications are provided.

In some embodiments, the invention is to provide biological activity and therapeutic uses of such GLP-1R/GCGR dual target agonist polypeptides in inhibition and improvement of non-alcoholic steatohepatitis and hepatic fibrosis including hepatic cirrhosis. The inventor has demonstrated that such GLP-1R/GCGR dual target agonist polypeptides can significantly inhibit activation of human hepatic stellate cells (LX-2) in vitro through a great number of experimental studies, suggesting that active polypeptides have excellent in vitro anti-hepatic fibrosis effect. Meanwhile, such polypeptides can significantly inhibit $CCl_4$-induced hepatic fibrosis in mice. In addition, such polypeptides can significantly improve high fat diet-induced fatty liver of mice as well as hepatic fatty degeneration and non-alcoholic adipositis of db/db diabetic mice.

In some embodiments, the invention is to provide biological activity and therapeutic uses of such GLP-1R/GCGR dual target agonist polypeptides in inhibition and improvement of fatty liver complicated by hepatic fibrosis. The inventor has demonstrated that such GLP-1R/GCGR dual target agonist polypeptides can significantly inhibit lipid and collagen deposition in livers of high fat diet-induced mice through a great number of experimental studies, suggesting that such polypeptides can inhibit fatty liver complicated by hepatic fibrosis.

In some embodiments, the invention is to provide biological activity and therapeutic uses of such GLP-1R/GCGR dual target agonist polypeptides in glucolipid metabolism adjustment and anti-hyperlipidemia. The inventor has demonstrated that such GLP-1R/GCGR dual target agonist polypeptides can significantly lower triglycerides (TG) level and total cholesterol (TC) level of db/db diabetic mice through a great number of experimental studies.

In some embodiments, the invention is to provide new therapeutic uses of such GLP-1R/GCGR dual target agonist polypeptides for indications.

Such GLP-1R/GCGR dual target agonist polypeptides are expected to be new generation of preventive or therapeutic drugs for such diseases as hyperlipemia, arteriosclerosis and non-alcoholic fatty liver diseases (including non-alcoholic fatty degeneration, non-alcoholic steatohepatitis, hepatic fibrosis and hepatic fibrosis complicated by hepatic cirrhosis).

The invention relates to GLP-1R/GCGR dual target agonist polypeptides comprising the parent peptide represented by the following amino acid sequence:
His-Xaa2-Gln-Gly-Thr-Phe-Thr-Ser-Asp-Xaa10-Ser-Lys-Xaa13-Leu-Asp-Xaa16-Xaa17-Xaa18-Ala-Xaa20-Xaa21-Phe-Xaa23-Xaa24-Trp-Leu-Xaa27-Xaa28-Xaa29-Xaa30-Xaa31-Xaa32-Xaa33-Xaa34-Xaa35-Xaa36-Xaa37-Xaa38-Xaa39-Xaa40-$COR_1$ (SEQ ID NO: 38)
wherein, $R_1$=—$NH_2$ or —OH;
Xaa2=Aib, Ser or D-Ser;
Xaa10=Lys or Tyr;
Xaa13=Lys or Tyr;
Xaa16=Ser, Aib, Lys or Glu;
Xaa17=Lys or Arg;
Xaa18=Arg or Ala;
Xaa20=His, Gln or Lys;
Xaa21=Asp or Glu;
Xaa23=Ile, Leu or Val;
Xaa24=Glu or Gln;
Xaa27=Met, Leu, Nle or is absent;
Xaa28=Ser, Asp, Asn, Arg or is absent;
Xaa29=Ala, Gly, Thr or is absent;
Xaa30=Gly or is absent;
Xaa31=Gly or is absent;
Xaa32=Pro or is absent;
Xaa33=Ser or is absent;
Xaa34=Ser or is absent;
Xaa35=Gly or is absent;
Xaa36=Ala or is absent;
Xaa37=Pro or is absent;
Xaa38=Pro or is absent;
Xaa39=Pro or is absent;
Xaa40=Ser or is absent.

In the amino acid sequence, at least one of Xaa10, Xaa16, Xaa17 or Xaa20 is Lys, the side chain of the at least one Lys or the Lys at position 12 is attached to a lipophilic substituent in such a way that a carboxyl group of the lipophilic substituent forms an amide bond with an amino group of a bridging group, the bridging group is attached to the parent peptide by means of a carboxyl group of the amino acid residue of the bridging group which forms an amide bond with a N-terminal residue of Lys of the parent peptide.

The bridging group is Glu, Asp, and/or (PEG)m, wherein m is an integer of 2-10; and the lipophilic substituent is an acyl group selected from $CH_3(CH_2)_nCO$— or $HOOC(CH_2)_nCO$—, wherein n is an integer of 10-24. The preferred bridging group may be Glu-$(PEG)_m$ or Asp-$(PEG)_m$ or $(PEG)_m$, which is attached in FIG. 16.

Preferred compounds of the invention are parent peptides comprising the following amino acid sequence:
His-Xaa2-Gln-Gly-Thr-Phe-Thr-Ser-Asp-Xaa10-Ser-Lys-Xaa13-Leu-Asp-Xaa16-Xaa17-Xaa18-Ala-Xaa20-Xaa21-Phe-Xaa23-Xaa24-Trp-Leu-Xaa27-Xaa28-Xaa29-Xaa30-Xaa31-Xaa32-Xaa33-Xaa34-Xaa35-Xaa36-Xaa37-Xaa38-Xaa39-Xaa40-$COR_1$ (SEQ ID NO: 38)
wherein, $R_1$=—$NH_2$;
Xaa2=Aib or D-Ser;
Xaa10=Lys or Tyr;
Xaa13=Lys or Tyr;
Xaa16=Ser, Aib, Glu or Lys;
Xaa17=Lys or Arg;
Xaa18=Arg or Ala;
Xaa20=His, Gln or Lys;
Xaa21=Asp or Glu;
Xaa23=Ile, Val;
Xaa24=Glu or Gln;
Xaa27=Met, Leu or Nle;

Xaa28=Asn, Asp, Arg or is absent;
Xaa29=Gly, Thr or is absent;
Xaa30=Gly or is absent;
Xaa31=Gly or is absent;
Xaa32=Pro or is absent;
Xaa33=Ser or is absent;
Xaa34=Ser or is absent;
Xaa35=Gly or is absent;
Xaa36=Ala or is absent;
Xaa37=Pro or is absent;
Xaa38=Pro or is absent;
Xaa39=Pro or is absent;
Xaa40=Ser or is absent.

The compounds of the invention are based on the theory that the intramolecular bridges can stabilize the helical structure of the molecule and so increase potency and/or selectivity at the GLP-1R or GCGR receptors. The compounds of the invention carry one or more intramolecular bridges within the sequence. Each such bridge is formed between the side chains of two amino acid residues which are typically separated by three amino acids in the linear sequence. For example, the bridge may be formed between the side chains of residue pairs 12 and 16, 16 and 20, 17 and 21, or 20 and 24. The two side chains can be linked to one another through ionic interactions, or by covalent bonds. Thus these pairs of residues may comprise oppositely charged side chains in order to form a salt bridge by ionic interactions. For example, one of the residues may be Glu or Asp, while the other residue may be Lys or Arg. The pairings of Lys and Glu as well as Lys and Asp may also be capable of reacting to form a lactam ring respectively.

The invention is also to provide a pharmaceutical composition comprising the GLP-1R/GCGR dual target agonist polypeptides of the invention. The pharmaceutical composition is prepared using the GLP-1R/GCGR dual target agonist polypeptides as an active ingredient added with pharmaceutically acceptable carriers and/or excipients.

The GLP-1R/GCGR dual target agonist polypeptides of the invention are effective in glucolipid metabolism adjustment and anti-hyperlipemia (significantly inhibiting triglyceride and total cholesterol), and can be used as drugs for prevention or treatment of hyperlipemia.

The GLP-1R/GCGR dual target agonist polypeptides of the invention are significantly effective in inhibition and improvement of hepatic fatty degeneration and non-alcoholic fatty liver diseases, and can be used as drugs for treatment of hepatic fatty degeneration and non-alcoholic steatohepatitis.

The GLP-1R/GCGR dual target agonist polypeptides of the invention are also significantly effective in inhibition and improvement of fatty liver complicated by hepatic fibrosis and cirrhosis, and can be used as drugs for treatment of hepatic fibrosis and cirrhosis.

The GLP-1R/GCGR dual target agonist polypeptides of the invention are potentially used as drugs for arteriosclerosis, atherosclerosis and coronary heart diseases.

In some embodiments, a method of preventing or treating non-alcoholic fatty liver diseases (NAFLDs), hyperlipemia, and/or arteriosclerosis in a subject can include administering to the subject at least one GLP-1R/GCGR dual target agonist polypeptide.

In some embodiments, a method of making a drug for preventing or treating non-alcoholic fatty liver diseases (NAFLDs), hyperlipemia and/or arteriosclerosis, can include preparing at least one GLP-1R/GCGR dual target agonist polypeptide.

The polypeptides of the invention are effective in improvement and treatment of hepatic fatty degeneration, non-alcoholic steatohepatitis, fatty liver complicated by hepatic fibrosis and cirrhosis and other non-alcoholic fatty liver diseases (NAFLD). The polypeptides of the invention can be used for direct or indirect therapy of any condition caused or characterized by non-alcoholic fatty liver diseases. The polypeptides of the invention are effective in improvement and treatment of hepatic fibrosis and cirrhosis. The polypeptides of the invention can be used for therapy of any condition caused or characterized by hepatic fibrosis and cirrhosis. The polypeptides of the invention have a beneficial regulating effect on circulating cholesterol level and triglyceride. Thus the polypeptides of the invention can also be used for direct or indirect therapy of any condition caused or characterized by hyperlipemia, for example, treatment or prevention of atherosclerosis, arteriosclerosis or coronary heart diseases.

The therapeutic effects of the polypeptides of the invention in these conditions may be as a result of or associated with their effect on liver and kidney as well as blood circulation system, or may be independent thereof.

The person skilled in the art can appreciate that the pharmaceutical composition of the invention is suitable for various administration routes, such as oral administration, percutaneous administration, intravenous administration, intramuscular administration, topical administration and intranasal administration. According to the used administration route, the pharmaceutical composition of the invention can be formulated into various suitable dosage forms, which comprises an effective amount of at least one polypeptide of the invention and at least one pharmaceutically acceptable pharmaceutical carrier.

Examples of suitable dosage forms are tablets, capsules, sugar coated tablets, granules, oral liquid and syrup, ointment and paste for the skin surface, aerosol, nasal spray and sterile solution for injection.

The pharmaceutical composition comprising the polypeptides of the invention may be prepared into solution or lyophilized powder for parenteral administration. Before use, an appropriate solvent or other pharmaceutically acceptable carrier can be added to reconfigure the powder, and liquid formula is generally buffer, osmotic solution and aqueous solution.

The dosage of the polypeptides of the invention in the pharmaceutical composition may vary in a wide range, which can be easily determined by the person skilled in this art according to certain factors such as the type of the disease, the severity of the disease, patient's body weight, the dosage form and the administration route.

The invention has the advantages of:
1) having better biological activity compared with GLP-1 analogues;
2) showing a significant prolonged half-life and better stability in pharmacokinetics experiment of the drug, having good stability, ease to be produced on large scale, and low cost;
3) having lower toxicity, larger safety window and smaller amount compared with small molecule compounds.

In particular embodiments, the following GLP-1R/GCGR dual target agonist polypeptides are related, having the following sequences:

Compound 1 (SEQ ID NO: 1):
His-(D-Ser)-Gln-Gly-Thr-Phe-Thr-Ser-Asp-Tyr-Ser-Lys(PEG$_2$-PEG$_2$-γGlu-CO(CH$_2$)$_{14}$CH$_3$)-Lys-Leu-Asp-Aib-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ H-(d-S)-QGTFTSDYS-K(PEG$_2$-PEG$_2$-γGlu-CO(CH$_2$)$_{14}$CH$_3$)-KLD-Aib-RRAQDFVQWLMNTGGPSSGAPPPS-NH$_2$ Compound 2 (SEQ ID NO: 2):
His-(D-Ser)-Gln-Gly-Thr-Phe-Thr-Ser-Asp-Tyr-Ser-Lys(PEG$_2$-PEG$_2$-CO(CH$_2$)$_{16}$CO$_2$H)-Lys-Leu-Asp-Aib-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ H-(d-S)-QGTFTSDYS-K(PEG$_2$-PEG$_2$-CO(CH$_2$)$_{16}$CO$_2$H)-KLD-Aib-RRAQDFVQWLMNTGGPSSGAPPPS-NH$_2$ Compound 3 (SEQ ID NO: 3):
His-(D-Ser)-Gln-Gly-Thr-Phe-Thr-Ser-Asp-Tyr-Ser-Lys(PEG$_2$-PEG$_2$-CO(CH$_2$)$_{16}$CH$_3$)-Lys-Leu-Asp-Aib-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ H-(d-S)-QGTFTSDYS-K(PEG$_2$-PEG$_2$-CO(CH$_2$)$_{16}$CH$_3$)-KLD-Aib-RRAQDFVQWLMNTGGPSSGAPPPS-NH$_2$ Compound 4 (SEQ ID NO: 4):
His-(D-Ser)-Gln-Gly-Thr-Phe-Thr-Ser-Asp-Lys(PEG$_2$-PEG$_2$-γGlu-CO(CH$_2$)$_{14}$CH$_3$)-Ser-Lys-Tyr-Leu-Asp-Aib-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ H-(d-S)-QGTFTSD-K(PEG$_2$-PEG$_2$-γGlu-CO(CH$_2$)$_{14}$CH$_3$)-SKYLD-Aib-RRAQDFVQWLMNTGGPSSGAPPPS Compound 5 (SEQ ID NO: 5):
His-(D-Ser)-Gln-Gly-Thr-Phe-Thr-Ser-Asp-Lys(PEG$_2$-PEG$_2$-γGlu-CO(CH2)$_{16}$CO$_2$H)-Ser-Lys-Tyr-Leu-Asp-Aib-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ H-(d-S)-QGTFTSD-K(PEG$_2$-PEG$_2$-γGlu-CO(CH$_2$)$_{16}$CO$_2$H)-SKYLD-Aib-RRAQDFVQWLMNTGGPSSGAPPPS-NH$_2$ Compound 6 (SEQ ID NO: 6):
His-(D-Ser)-Gln-Gly-Thr-Phe-Thr-Ser-Asp-Tyr-Ser-Lys-Tyr-Leu-Asp-Lys(PEG$_2$-PEG$_2$-γGlu-CO(CH$_2$)$_{14}$CH$_3$)-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ H-(d-S)-QGTFTSDYSKYLD-K(PEG$_2$-PEG$_2$-γGlu-CO(CH$_2$)$_{14}$CH$_3$)-RRAQDFVQWLMNTGGPSSGAPPPS-NH$_2$ Compound 7 (SEQ ID NO: 7):
His-(D-Ser)-Gln-Gly-Thr-Phe-Thr-Ser-Asp-Tyr-Ser-Lys-Tyr-Leu-Asp-Aib-Lys(PEG$_2$-PEG$_2$-γGlu-CO(CH$_2$)$_{16}$CO$_2$H)-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ H-(d-S)-QGTFTSDYSKYLD-Aib-K(PEG$_2$-PEG$_2$-γGlu-CO(CH$_2$)$_{16}$CO$_2$H)-RAQDFVQWLMNTGGPSSGAPPPS-NH$_2$ Compound 8 (SEQ ID NO: 8):
His-Aib-Gln-Gly-Thr-Phe-Thr-Ser-Asp-Lys(PEG$_2$-PEG$_2$-γGlu-CO(CH$_2$)$_{14}$CH$_3$)-Ser-Lys-Tyr-Leu-Asp-Aib-Arg-Arg-Ala-Gln-Asp-Phe-Val-Gln-Trp-Leu-Leu-Asp-Gly-Gly-Pro-Ser-Ser-Gly-Ala-Pro-Pro-Pro-Ser-NH$_2$ H-Aib-QGTFTSD-K(PEG$_2$-PEG$_2$-γGlu-CO(CH$_2$)$_{14}$CH$_3$)-SKYLD-Aib-RRAQDFVQWLLDGGPSSGAPPPS-NH$_2$ Compound 9 (SEQ ID NO: 9):
His-(D-Ser)-Gln-Gly-Thr-Phe-Thr-Ser-Asp-Tyr-Ser-Lys(PEG$_2$-PEG$_2$-CO(CH$_2$)$_{14}$CH$_3$)-Lys-Leu-Asp-Aib-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ H-(d-S)-QGTFTSDYS-K(PEG$_2$-PEG$_2$-CO(CH$_2$)$_{14}$CH$_3$)-KLD-Aib-RRAQDFVQWLMNTGGPSSGAPPPS-NH$_2$ Compound 10 (SEQ ID NO: 10):
His-(D-Ser)-Gln-Gly-Thr-Phe-Thr-Ser-Asp-Tyr-Ser-Lys-Tyr-Leu-Asp-Aib-Lys(PEG$_2$-PEG$_2$-CO(CH$_2$)$_{16}$CO$_2$H)-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ H-(d-S)-QGTFTSDYSKYLD-Aib-K(PEG$_2$-PEG$_2$-CO(CH$_2$)$_{16}$CO$_2$H)-RAQDFVQWLMNTGGPSSGAPPPS-NH$_2$ Compound 11 (SEQ ID NO: 11):
His-Aib-Gln-Gly-Thr-Phe-Thr-Ser-Asp-Lys(PEG$_2$-PEG$_2$-γGlu-CO(CH$_2$)$_{14}$CO$_2$H)-Ser-Lys-Tyr-Leu-Asp-Aib-Arg-Arg-Ala-Gln-Asp-Phe-Val-Gln-Trp-Leu-Leu-Asp-Gly-Gly-Pro-Ser-Ser-Gly-Ala-Pro-Pro-Pro-Ser-NH$_2$ H-Aib-QGTFTSD-K(PEG$_2$-PEG$_2$-γGlu-CO(CH$_2$)$_{14}$CO$_2$H)-SKYLD-Aib-RRAQDFVQWLLDGGPSSGAPPPS-NH$_2$ Compound 12 (SEQ ID NO: 12):
His-Aib-Gln-Gly-Thr-Phe-Thr-Ser-Asp-Lys(PEG$_2$-PEG$_2$-γGlu-CO(CH$_2$)$_{16}$CH$_3$)-Ser-Lys-Tyr-Leu-Asp-Aib-Arg-Arg-Ala-Gln-Asp-Phe-Val-Gln-Trp-Leu-Leu-Asp-Gly-Gly-Pro-Ser-Ser-Gly-Ala-Pro-Pro-Pro-Ser-NH$_2$ H-Aib-QGTFTSD-K(PEG$_2$-PEG$_2$-γGlu-CO(CH$_2$)$_{16}$CH$_3$)-SKYLD-Aib-RRAQDFVQWLLDGGPSSGAPPPS-NH$_2$ Compound 13 (SEQ ID NO: 13):
His-Aib-Gln-Gly-Thr-Phe-Thr-Ser-Asp-Lys(PEG$_2$-PEG$_2$-γGlu-CO(CH$_2$)$_{14}$CO$_2$H)-Ser-Lys-Tyr-Leu-Asp-Glu-Arg-Arg-Ala-Gln-Asp-Phe-Val-Gln-Trp-Leu-Leu-Asp-Gly-Gly-Pro-Ser-Ser-Gly-Ala-Pro-Pro-Pro-Ser-NH$_2$ H-Aib-QGTFT SD-K(PEG$_2$-PEG$_2$-γGlu-CO(CH$_2$)$_{14}$CO$_2$H)-SKYLDERRAQDFVQWLLDGGPSSGAPPPS-NH$_2$ Compound 14 (SEQ ID NO: 14):
His-Aib-Gln-Gly-Thr-Phe-Thr-Ser-Asp-Lys(PEG$_2$-PEG$_2$-γGlu-CO(CH$_2$)$_{16}$CH$_3$)-Ser-Lys-Tyr-Leu-Asp-Glu-Arg-Arg-Ala-Gln-Asp-Phe-Val-Gln-Trp-Leu-Leu-Asp-Gly-Gly-Pro-Ser-Ser-Gly-Ala-Pro-Pro-Pro-Ser-NH$_2$ H-Aib-QGTFTSD-K(PEG$_2$-PEG$_2$-γGlu-CO(CH$_2$)$_{16}$CH$_3$)-SKYLDERRAQDFVQWLLDGGPSSGAPPPS-NH$_2$ Compound 15 (SEQ ID NO: 15):
His-Aib-Gln-Gly-Thr-Phe-Thr-Ser-Asp-Lys(PEG$_2$-PEG$_2$-γGlu-CO(CH$_2$)$_{16}$CO$_2$H)-Ser-Lys-Tyr-Leu-Asp-Glu-Arg-Arg-Ala-Gln-Asp-Phe-Val-Gln-Trp-Leu-Leu-Asp-Gly-Gly-Pro-Ser-Ser-Gly-Ala-Pro-Pro-Pro-Ser-NH$_2$ H-Aib-QGTFT SD-K(PEG$_2$-PEG$_2$-γGlu-CO(CH$_2$)$_{16}$CO$_2$H)-SKYLDERRAQDFVQWLLDGGPSSGAPPPS-NH$_2$ Compound 16 (SEQ ID NO: 16):
His-Aib-Gln-Gly-Thr-Phe-Thr-Ser-Asp-Lys(PEG$_2$-PEG$_2$-γGlu-CO(CH$_2$)$_{14}$CH$_3$)-Ser-Lys-Tyr-Leu-Asp-Glu-Arg-Arg-Ala-Gln-Asp-Phe-Val-Gln-Trp-Leu-Leu-Asp-Gly-Gly-Pro-Ser-Ser-Gly-Ala-Pro-Pro-Pro-Ser-NH$_2$ H-Aib-QGTFTSD-K(PEG$_2$-PEG$_2$-γGlu-CO(CH$_2$)$_{14}$CH$_3$)-SKYLDERRAQDFVQWLLDGGPSSGAPPPS-NH$_2$ Compound 17 (SEQ ID NO: 17):
His-(D-Ser)-Gln-Gly-Thr-Phe-Thr-Ser-Asp-Tyr-Ser-Lys-Tyr-Leu-Asp-Ser-Lys(PEG$_2$-PEG$_2$-γGlu-CO(CH$_2$)$_{16}$CO$_2$H)-Ala-Ala-His-Asp-Phe-Val-Glu-Trp-Leu-Leu-Arg-Ala-NH$_2$ H-(d-S)-QGTFTSDYSKYLDS-K(PEG$_2$-PEG$_2$-γGlu-CO(CH$_2$)$_{16}$CO$_2$H)-AAHDFVEWLLRA-NH$_2$ Compound 18 (SEQ ID NO: 18):
His-(D-Ser)-Gln-Gly-Thr-Phe-Thr-Ser-Asp-Tyr-Ser-Lys-Tyr-Leu-Asp-Glu-Lys-Ala-Ala-Lys(PEG$_2$-PEG$_2$-γGlu-CO(CH$_2$)$_{16}$CO$_2$H)-Glu-Phe-Ile-Glu-Trp-Leu-Leu-Arg-Ala-NH$_2$ H-(d-S)-QGTFTSDYSKYLDEKAA-K(PEG$_2$-PEG$_2$-γGlu-CO(CH$_2$)$_{16}$CO$_2$H)-EFIEWLLRA-NH$_2$ -continued Compound 19 (SEQ ID NO: 19):
His-Aib-Gln-Gly-Thr-Phe-Thr-Ser-Asp-Lys(PEG$_2$-PEG$_2$-γGlu-CO(CH$_2$)$_{16}$CO$_2$H)-Ser-Lys-Tyr-Leu-Asp-Aib-Arg-Arg-Ala-Gln-Asp-Phe-Val-Gln-Trp-Leu-Leu-Asp-Gly-Gly-Pro-Ser-Ser-Gly-Ala-Pro-Pro-Pro-Ser-NH$_2$ H-Aib-QGTFTSD-K(PEG$_2$-PEG$_2$-γGlu-CO(CH$_2$)$_{16}$CO$_2$H)-SKYLD-Aib-RRAQDFVQWLLDGGPSSGAPPPS-NH$_2$ Compound 20 (SEQ ID NO: 20):
His-(D-Ser)-Gln-Gly-Thr-Phe-Thr-Ser-Asp-Tyr-Ser-Lys(PEG$_2$-PEG$_2$-γGlu-CO(CH2)$_{16}$CO$_2$H)-Lys-Leu-Asp-Aib-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ H-(d-S)-QGTFTSDYS-K(PEG$_2$-PEG$_2$-γGlu-CO(CH$_2$)$_{16}$CO$_2$H)-KLD-Aib-RRAQDFVQWLMNTGGPSSGAPPPS-NH$_2$ Compound 21 (SEQ ID NO: 21):
His-(D-Ser)-Gln-Gly-Thr-Phe-Thr-Ser-Asp-Tyr-Ser-Lys-Tyr-Leu-Asp-Ser-Lys(PEG$_2$-PEG$_2$-γGlu-CO(CH$_2$)$_{16}$CO$_2$H)-Ala-Ala-His-Asp-Phe-Val-Glu-Trp-Leu-Leu-Asn-Gly-Gly-Pro-Ser-Ser-Gly-Ala-Pro-Pro-Pro-Ser-NH$_2$ H-(d-S)-QGTF TSDYSKYLDS-K(PEG$_2$-PEG$_2$-γGlu-CO(CH$_2$)$_{16}$CO$_2$H)-AAHDFVEWLLNGGPSSGAPPPS-NH$_2$ Compound 22 (SEQ ID NO: 22):
His-(D-Ser)-Gln-Gly-Thr-Phe-Thr-Ser-Asp-Tyr-Ser-Lys-Tyr-Leu-Asp-Ser-Lys(PEG$_2$-PEG$_2$-γGlu-CO(CH$_2$)$_{16}$CH$_3$)-Ala-Ala-His-Asp-Phe-Val-Glu-Trp-Leu-Leu-Asn-Gly-Gly-Pro-Ser-Ser-Gly-Ala-Pro-Pro-Pro-Ser-NH$_2$ H-(d-S)-QGTFTSDYSKYLDS-K(PEG$_2$-PEG$_2$-γGlu-CO(CH$_2$)$_{16}$CH$_3$)-AAHDFVEWLLNGGPSSGAPPPS-NH$_2$ Compound 23 (SEQ ID NO: 23):
His-(D-Ser)-Gln-Gly-Thr-Phe-Thr-Ser-Asp-Tyr-Ser-Lys-Tyr-Leu-Asp-Glu-Lys-Ala-Ala-Lys(PEG$_2$-PEG$_2$-γGlu-CO(CH$_2$)$_{14}$CH$_3$)-Glu-Phe-Ile-Glu-Trp-Leu-Leu-Arg-Ala-NH$_2$ H-(d-S)-QGTFTSDYSKYLDEKAA-K(PEG$_2$-PEG$_2$-γGlu-CO(CH$_2$)$_{14}$CH$_3$)-EFIEWLLRA-NH$_2$ Compound 24 (SEQ ID NO: 24):
His-(D-Ser)-Gln-Gly-Thr-Phe-Thr-Ser-Asp-Tyr-Ser-Lys-Tyr-Leu-Asp-Glu-Lys-Ala-Ala-Lys(PEG$_2$-PEG$_2$-γGlu-CO(CH2)$_{16}$CH$_3$)-Glu-Phe-Ile-Glu-Trp-Leu-Leu-Arg-Ala-NH$_2$ H-(d-S)-QGTFTSDYSKYLDEKAA-K(PEG$_2$-PEG$_2$-γGlu-CO(CH$_2$)$_{16}$CH$_3$)-EFIEWLLRA-NH$_2$ Compound 25 (SEQ ID NO: 25):
His-(D-Ser)-Gln-Gly-Thr-Phe-Thr-Ser-Asp-Tyr-Ser-Lys-Tyr-Leu-Asp-Ser-Lys(PEG$_2$-PEG$_2$-γGlu-CO(CH$_2$)$_{16}$CH$_3$)-Ala-Ala-His-Asp-Phe-Val-Glu-Trp-Leu-Leu-Arg-Ala-NH$_2$ H-(d-S)-QGTFTSDYSKYLDS-K(PEG$_2$-PEG$_2$-γGlu-CO(CH$_2$)$_{16}$CH$_3$)-AAHDFVEWLLRA-NH$_2$ Compound 26 (SEQ ID NO: 26):
His-(D-Ser)-Gln-Gly-Thr-Phe-Thr-Ser-Asp-Tyr-Ser-Lys-Tyr-Leu-Asp-Glu-Lys-Ala-Ala-Lys(PEG$_2$-PEG$_2$-γGlu-CO(CH$_2$)$_{16}$CO$_2$H)-Glu-Phe-Ile-Glu-Trp-Leu-Leu-Asn-Gly-Gly-Pro-Ser-Ser-Gly-Ala-Pro-Pro-Pro-Ser-NH$_2$ H-(d-S)-QGTFTSDYSKYLDEKAA-K(PEG$_2$-PEG$_2$-γGlu-CO(CH$_2$)$_{16}$CO$_2$H)-EFIEWLLNGGPSSGAPPPS-NH$_2$ Compound 27 (SEQ ID NO: 27):
His-(D-Ser)-Gln-Gly-Thr-Phe-Thr-Ser-Asp-Tyr-Ser-Lys-Tyr-Leu-Asp-Glu-Lys-Ala-Ala-Lys(PEG$_2$-PEG$_2$-γGlu-CO(CH$_2$)$_{14}$CO$_2$H)-Glu-Phe-Ile-Glu-Trp-Leu-Leu-Asn-Gly-Gly-Pro-Ser-Ser-Gly-Ala-Pro-Pro-Pro-Ser-NH$_2$ H-(d-S)-QGTFTSDYSKYLDEKAA-K(PEG$_2$-PEG$_2$-γGlu-CO(CH$_2$)$_{14}$CO$_2$H)-EFIEWLLNGGPSSGAPPPS-NH$_2$ Compound 28 (SEQ ID NO: 28):
His-(D-Ser)-Gln-Gly-Thr-Phe-Thr-Ser-Asp-Tyr-Ser-Lys-Tyr-Leu-Asp-Glu-Lys-Ala-Ala-Lys(PEG$_2$-PEG$_2$-γGlu-CO(CH$_2$)$_{16}$CH$_3$)-Glu-Phe-Ile-Glu-Trp-Leu-Leu-Asn-Gly-Gly-Pro-Ser-Ser-Gly-Ala-Pro-Pro-Pro-Ser-NH$_2$ H-(d-S)-QGTFTSDYSKYLDEKAA-K(PEG$_2$-PEG$_2$-γGlu-CO(CH$_2$)$_{16}$CH$_3$)-EFIEWLLNGGPSSGAPPPS-NH$_2$ Compound 29 (SEQ ID NO: 29):
His-(D-Ser)-Gln-Gly-Thr-Phe-Thr-Ser-Asp-Tyr-Ser-Lys-Tyr-Leu-Asp-Glu-Lys-Ala-Ala-Lys(PEG$_2$-PEG$_2$-γGlu-CO(CH$_2$)$_{14}$CH$_3$)-Glu-Phe-Ile-Glu-Trp-Leu-Leu-Asn-Gly-Gly-Pro-Ser-Ser-Gly-Ala-Pro-Pro-Pro-Ser-NH$_2$ H-(d-S)-QGTFTSDYSKYLDEKAA-K(PEG$_2$-PEG$_2$-γGlu-CO(CH$_2$)$_{14}$CH$_3$)-EFIEWLLNGGPSSGAPPPS-NH$_2$ Compound 30 (SEQ ID NO: 30):
His-(D-Ser)-Gln-Gly-Thr-Phe-Thr-Ser-Asp-Lys(PEG$_2$-PEG$_2$-CO(CH$_2$)$_{16}$CO$_2$H)-Soer-Lys-Tyr-Leu-Asp-Aib-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ H-(d-S)-QGTFTSD-K(PEG$_2$-PEG$_2$-CO(CH$_2$)$_{16}$CO$_2$H)-SKYLD-Aib-RRAQDFVQWLMNTGGPSSGAPPPS-NH$_2$ Compound 31 (SEQ ID NO: 31):
His-(D-Ser)-Gln-Gly-Thr-Phe-Thr-Ser-Asp-Lys(PEG$_2$-PEG$_2$-CO(CH$_2$)$_{14}$CH$_3$)-Ser-Lys-Tyr-Leu-Asp-Aib-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ H-(d-S)-QGTFTSD-K(PEG$_2$-PEG$_2$-CO(CH2)$_{14}$CH$_3$)-SKYLD-Aib-RRAQDFVQWLMNTGGPSSGAPPPS-NH$_2$ Compound 32 (SEQ ID NO: 32):
His-(D-Ser)-Gln-Gly-Thr-Phe-Thr-Ser-Asp-Lys(PEG$_2$-PEG$_2$-CO(CH$_2$)$_{16}$CH$_3$)-Ser-Lys-Tyr-Leu-Asp-Aib-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ H-(d-S)-QGTFTSD-K(PEG$_2$-PEG$_2$-CO(CH$_2$)$_{16}$CH$_3$)-SKYLD-Aib-RRAQDFVQWLMNTGGPSSGAPPPS-NH$_2$ Compound 33 (SEQ ID NO: 33):
His-(D-Ser)-Gln-Gly-Thr-Phe-Thr-Ser-Asp-Tyr-Ser-Lys-Tyr-Leu-Asp-Aib-Lys(PEG$_2$-PEG$_2$-γGlu-CO(CH$_2$)$_{14}$CH$_3$)-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ H-(d-S)-QGTFTSDYSKYLD-Aib-K(PEG$_2$-PEG$_2$-γGlu-CO(CH$_2$)$_{14}$CH$_3$)-RAQDFVQWLMNTGGPSSGAPPPS-NH$_2$ Compound 34 (SEQ ID NO: 34):
His-(D-Ser)-Gln-Gly-Thr-Phe-Thr-Ser-Asp-Tyr-Ser-Lys-Tyr-Leu-Asp-Lys(PEG$_2$-PEG$_2$-γGlu-CO(CH$_2$)$_{16}$CO$_2$H)-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ H-(d-S)-QGTFTSDYSKYLD-K(PEG$_2$-PEG$_2$-γGlu-CO(CH$_2$)$_{16}$CO$_2$H)-RRAQDFVQWLMNTGGPSSGAPPPS-NH$_2$ Compound 35 (SEQ ID NO: 35):
His-(D-Ser)-Gln-Gly-Thr-Phe-Thr-Ser-Asp-Tyr-Ser-Lys-Tyr-Leu-Asp-Lys(PEG$_2$-PEG$_2$-CO(CH$_2$)$_{16}$CO$_2$H)-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ H-(d-S)-QGTFTSDYSKYLD-K(PEG$_2$-PEG$_2$-CO(CH$_2$)$_{16}$CO$_2$H)-RRAQDFVQWLMNTGGPSSGAPPPS-NH$_2$ Compound 36 (SEQ ID NO: 36):
His-(D-Ser)-Gln-Gly-Thr-Phe-Thr-Ser-Asp-Tyr-Ser-Lys-Tyr-Leu-Asp-Lys(PEG$_2$-PEG$_2$-γGlu-CO(CH$_2$)$_{16}$CH$_3$)-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ H-(d-S)-QGTFTSDYSKYLD-K(PEG$_2$-PEG$_2$-γGlu-CO(CH$_2$)$_{16}$CH$_3$)-RRAQDFVQWLMNTGGPSSGAPPPS-NH$_2$

```
Compound 37 (SEQ ID NO: 37):
His-(D-Ser)-Gln-Gly-Thr-Phe-Thr-Ser-Asp-Tyr-Ser-Lys-Tyr-Leu-Asp-Lys(PEG2-PEG2-γGlu-
CO(CH2)14CH3)-Arg-Arg-Ala-Gln-Asp-Phe-Val-Gln-Trp-Leu-Nle-Asn-Thr-Gly-Gly-Pro-Ser-
Ser-Gly-Ala-Pro-Pro-Pro-Ser-NH2

H-(d-S)-QGTFTSDYSKYLD-K(PEG2-PEG2-γGlu-CO(CH2)14CH3)-RRAQDFVQWL-Nle-NTGGPSSGAPPPS-NH2
```

In the above sequences, Lys modification may be one of the following structures:

Lys(PEG$_2$-PEG$_2$—CO(CH$_2$)$_{14}$CH$_3$):

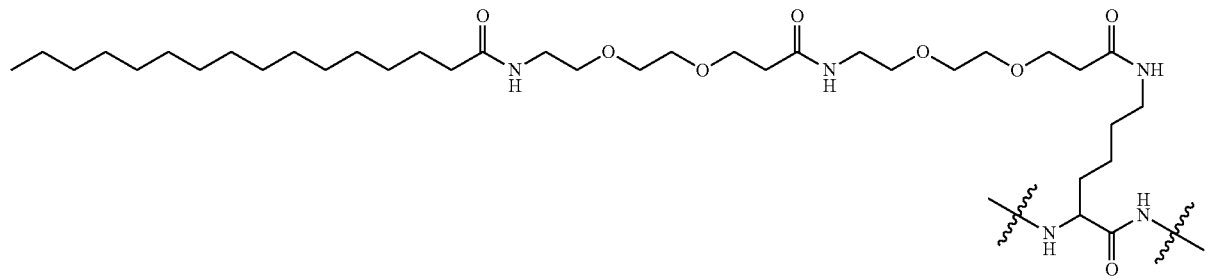

Lys(PEG$_2$-PEG$_2$-γGlu-CO(CH$_2$)$_{14}$CH$_3$):

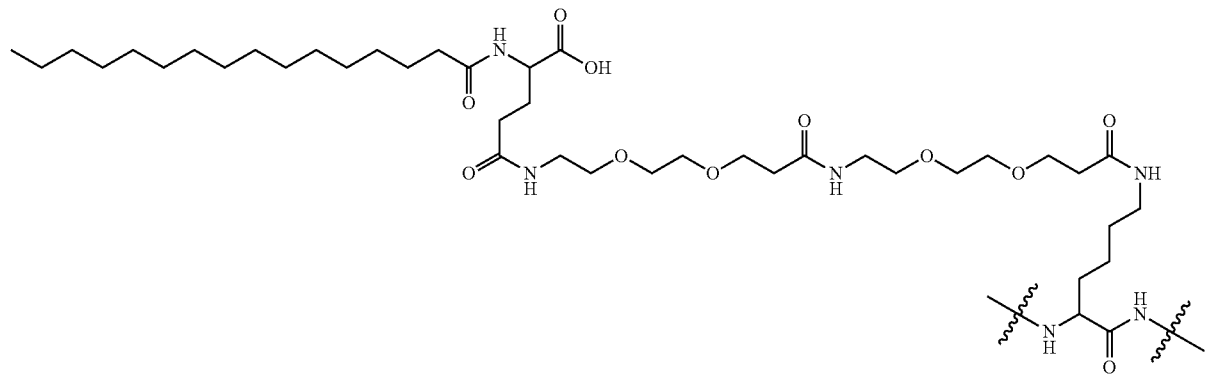

Lys(PEG$_2$-PEG$_2$—CO(CH$_2$)$_{14}$CO$_2$H):

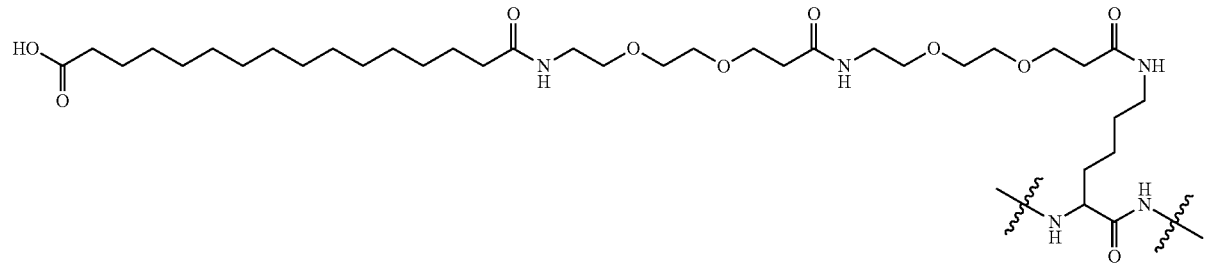

Lys(PEG₂-PEG₂-γGlu-CO(CH₂)₁₄CO₂H):
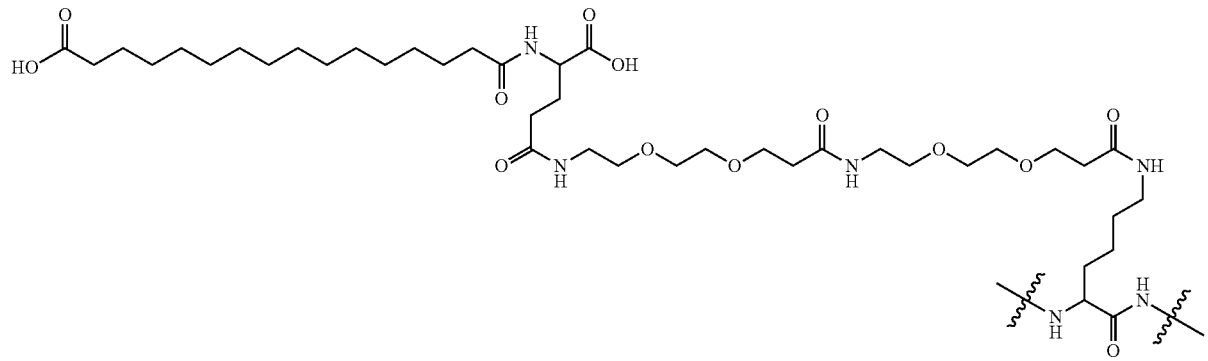
Lys(PEG₂-PEG₂—CO(CH₂)₁₆CO₂H):
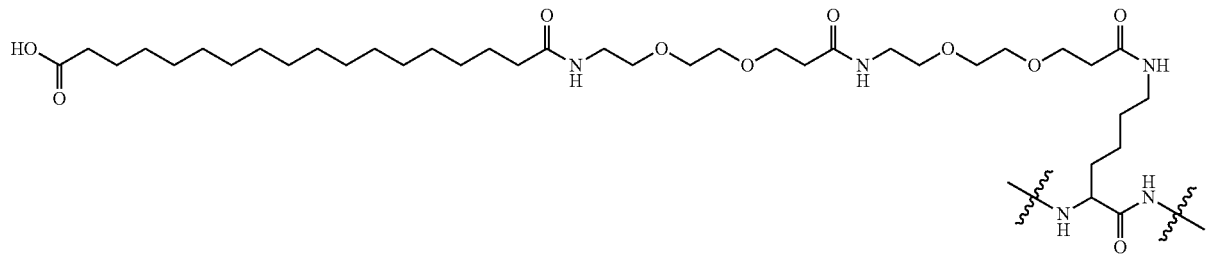
Lys(PEG₂-PEG₂-γGlu-CO(CH₂)₁₆CO₂H):
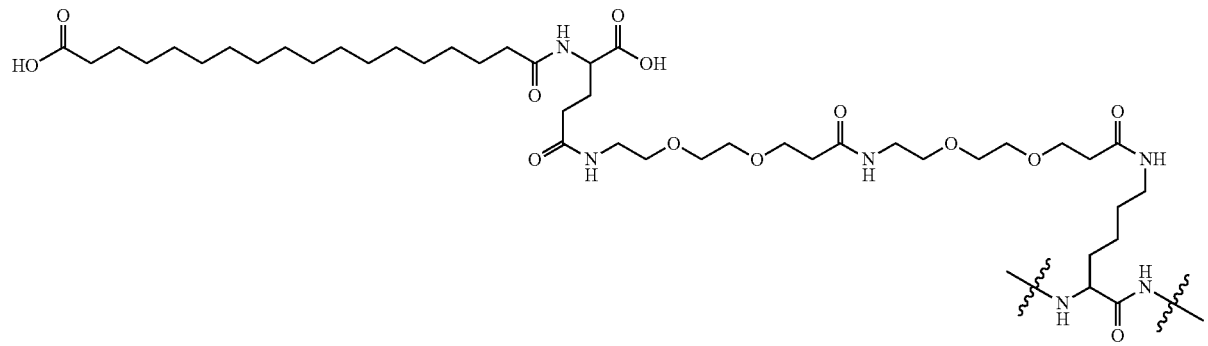
Lys(PEG₂-PEG₂—CO(CH₂)₁₆CH₃):
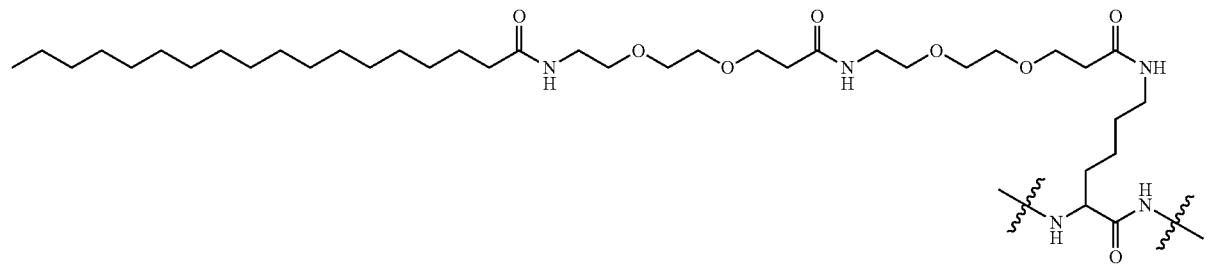

Lys(PEG$_2$-PEG$_2$-γGlu-CO(CH$_2$)$_{16}$CH$_3$):

-continued

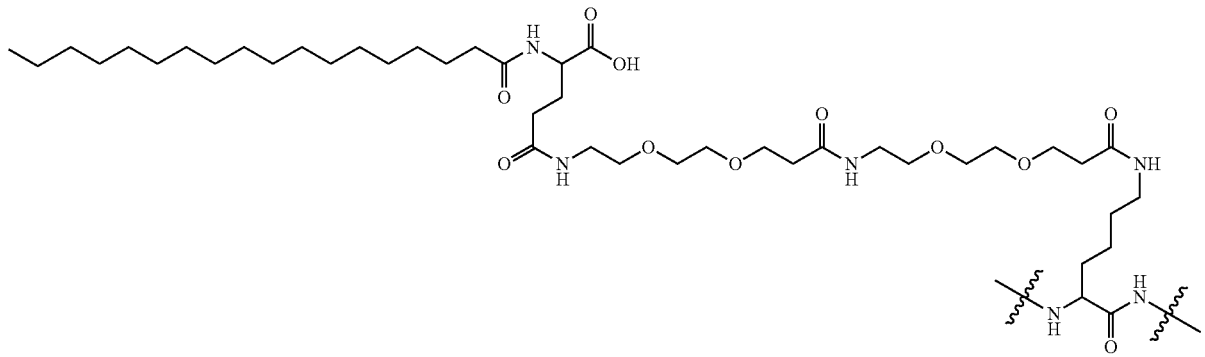

The Lys in the modification structures may be replaced with:

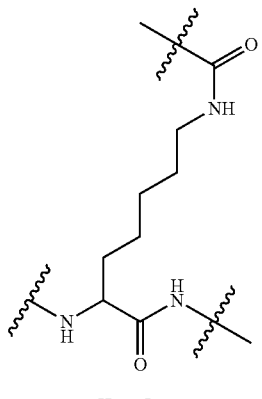

HomoLys

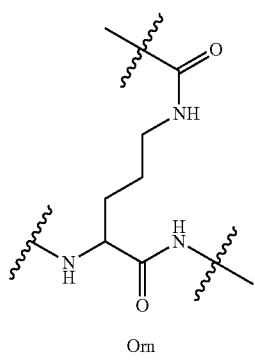

Orn

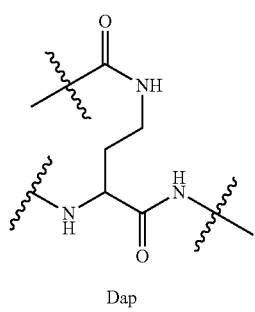

Dap

-continued

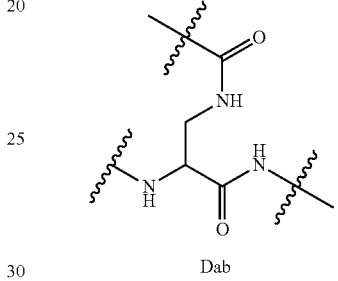

Dab

The abbreviations used in the invention are defined as follows:

Boc is tert-butyloxycarbonyl, Fmoc is fluorenylmethoxy-carbonyl, t-Bu is tert-butyl, ivDDe is 1-(4,4-dimethyl-2,6-dioxo-cycl ohexylidene)-3-methyl-butyl removal and lipophilic substituent, resin is resin, TFA is trifluoroacetic acid, EDT is 1,2-ethanedithiol, Phenol is phenol, FBS is fetal bovine serum, BSA is bovine serum albumin, HPLC is high performance liquid chromatography, GLP-1R is glucagon-like peptide-1 receptor, GCGR is glucagon receptor, GLP-1 is glucagon-like peptide, mPEG is mono-methoxy-polyethylene diol, OXM is oxyntomodulin, His is histidine, Ser is serine, D-Ser is D-serine, Gln is glutamine, Gly is glycine, Glu is glutamic acid, Ala is alanine acid, Thr is threonine, Lys is lysine, Arg is arginine, Tyr is tyrosine, Asp is aspartic acid, Trp is tryptophan, Phe is phenylalanine, Ile is isoleucine, Leu is leucine, Cys is cysteine, Pro is proline, Val is valine, Met is methionine, Asn is asparagines, HomoLys is homolysine, Orn is ornithine, Dap is diaminopimelic acid, Dab is 2,4-diaminobutyric acid, Nle is norleucine, and Aib is 2-aminoisobutyric acid.

DETAILED DESCRIPTION OF THE INVENTION

Figure 1:
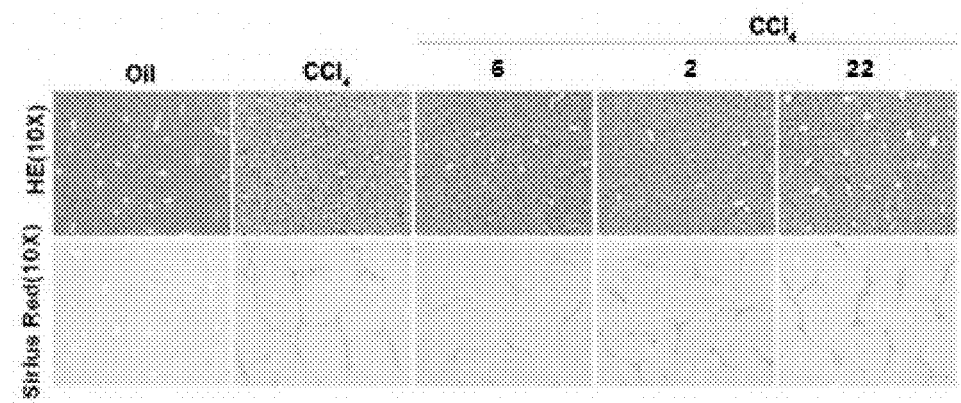
FIG. 1 shows the immunohistochemical staining results of hepatic tissue sections, which are caused by the application of the compounds 2, 6 and 22 to CCl$_4$-induced hepatic fibrosis mice.

The embodiments of the invention will be described in detail hereafter in conjunction with the examples, but those skilled in the art will appreciate that the following examples are only intended to indicate the invention and shall not be deemed to define the scope of the invention. Unless otherwise specified, the examples were carried out according to conventional conditions or the conditions recommended by manufacturers. The reagents or instruments used, the manufacture of which were not specified, were all conventional products can be obtained commercially.

Example 1

Synthesis of Polypeptide Compound

Materials:

All amino acids were purchased from NovaBiochem Company. Unless otherwise specified, all other reagents were analytically pure and purchased from Sigma Company. Protein Technologies PRELUDE 6-channel polypeptide synthesizer was used. Phenomenex Luna C18 preparative column (46 mm×250 mm) was used for purification of the polypeptides. High performance liquid chromatograph was manufactured by Waters Company. MS analysis was determined using Agilent mass spectrometer.

Synthetic method of polypeptide compounds of the invention is illustrated by taking the polypeptide compound 6 (SEQ ID NO: 6) as an example:

Structure sequence (SEQ ID NO: 6):

His-(D-Ser)-Gln-Gly-Thr-Phe-Thr-Ser-Asp-Tyr-Ser-Lys-Tyr-Leu-Asp-Lys(PEG$_2$-PEG$_2$-$_\gamma$Glu-CO(CH$_2$)$_{14}$CH$_3$)-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ a) Main peptide chain assembly:

The following polypeptide in a scale of 0.25 mmol was synthesized on a CS336X peptide synthesizer (CS Bio American Company) according to Fmoc/t-Bu strategy:

Boc-His(Boc)-D-Ser(t-Bu)-Gln(OtBu)-Gly-Thr(t-Bu)-Phe-Thr(t-Bu)-Ser(tBu)-Asp(OtBu)-Tyr(t-Bu)-Ser(t-Bu)-Lys(Boc)-Tyr(t-Bu)-Leu-Asp(OtBu)-Lys(ivDde)-Arg(Pbf)-Arg(Pbf)-Ala-Gln(Trt)-Asp(OtBu)-Phe-Val-Gln(Trt)-Trp(Boc)-Leu-Met-n(Trt)-Thr(t-Bu)-Gly-Gly-Pro-Ser(t-Bu)-Ser(t-Bu)-Gly-Ala-Pro-Pro-Pro-Ser(t-Bu)-rink amide resin (1) Step 1: 0.75 g of Rink amide MBHA-LL resin (Novabiochem, loading 0.34 mmol/g) was swelled in dichloromethane (DCM) for 1 hour, and the resin was fully washed with N,N-dimethylformamide (DMF) for three times (2) Step 2: The procedure reaction was performed using Rink amide resin as carrier, the mixture of 6-chloro-benzotriazole-1,1,3,3-tetramethyluronium hexafluorophosphate (HCTU), organic base N,N-diisopropylethylamine (DIEPA) at a molar ratio of 1:1 as coupling agent, and N,N-dimethylformamide (DMF) as solvent, the condensation reactions were performed to successively link.

Fmoc-Ser(t-Bu)-OH, Fmoc-Pro-OH (3x), Fmoc-Ala-OH, Fmoc-Gly-OH, Fmoc-Ser(t-Bu)-OH (2x), Fmoc-Pro-OH, Fmoc-Gly-OH (2x), Fmoc-Thr(t-Bu)-OH, Fmoc-Asn(Trt)-OH, Fmoc-Met-OH, Fmoc-Leu-OH, Fmoc-Trp(Boc)-OH, Fmoc-Glu(OtBu)-OH, Fmoc-Val-OH, Fmoc-Phe-OH, Fmoc-Asp(OtBu)-OH, Fmoc-Gln(Trt)-OH, Fmoc-Ala-OH, Fmoc-Arg(Pbf)-OH (2x), Fmoc-Lys(ivDde)-OH, Fmoc-Asp(OtBu)-OH, Fmoc-Leu-OH, Fmoc-Tyr(t-Bu)-OH, Fmoc-Lys(Boc)-OH, Fmoc-Ser(t-Bu)-OH, Fmoc-Tyr(t-Bu)-OH, Fmoc-Asp(OtBu)-OH, Fmoc-Ser(t-Bu)-OH, Fmoc-Thr(t-Bu)-OH, Fmoc-Phe-OH, Thr(t-Bu)-OH, Fmoc-Gly-OH, Fmoc-Gln(Trt)-OH, Fmoc-D-Ser(t-Bu)-OH, Boc-His(Boc)-OH to obtain:

Boc-His(Boc)-D-Ser(t-Bu)-Gln(OtBu)-Gly-Thr(t-Bu)-Phe-Thr(t-Bu)-Ser(tBu)-Asp(OtBu)-Tyr(t-Bu)-Ser(t-Bu)-Lys(Boc)-Tyr(t-Bu)-Leu-Asp(OtBu)-Lys(ivDde)-Arg(Pbf)-Arg(Pbf)-Ala-Gln(Trt)-Asp(OtBu)-Phe-Val-Gln(Trt)-Trp(Boc)-Leu-Met-Asn(Trt)-Thr(t-Bu)-Gly-Gly-Pro-Ser(t-Bu)-Ser(t-Bu)-Gly-Ala-Pro-Pro-Pro-Ser(t-Bu)-rink amide resin. Subsequently, the resin was fully washed with N,N-dimethylformamide (DMF), dichloromethane (DCM), Methanol, dichloromethane (DCM), and N,N-dimethylformamide (DMF) in sequence for three times respectively.

In the reaction, 1) the amount of the first amino acid Fmoc-Ser(t-Bu)-OH and the amount of the resin was at a ratio of 1:1~6:1; and 2) in each of the subsequent condensation reactions, each of the amount of Fmoc protected amino acid, 6-chloro-benzotriazole-1,1,3,3-tetramethyluronium hexafluorophosphate (HCTU), organic base N,N-diisopropylethylamine (DIEPA) was excess by 2-8 times, the reaction time was 1-5 hours.

b) Removal of 1-(4,4-dimethyl-2,6-dioxo-cyclohexylidene)-3-methyl-butyl (ivDde) and introduction of lipophilic substituent:

The resin was washed twice in the solution of N,N-dimethylformamide (DMF)/dichloromethane (DCM)=1:1 (volume ratio), and added with freshly prepared 3.0% hydrazine hydrate in N,N-dimethylformamide (DMF). The reaction mixture was shaken at room temperature for 10-30 minutes, and then filtered. The hydrazine treatment step was repeated five times to obtain:

Boc-His(Boc)-D-Ser(t-Bu)-Gln(OtBu)-Gly-Thr(t-Bu)-Phe-Thr(t-Bu)-Ser(tBu)-Asp(OtBu)-Tyr(t-Bu)-Ser(t-Bu)-Lys(Boc)-Tyr(t-Bu)-Leu-Asp(OtBu)-Lys-Arg(Pbf)-Arg(Pbf)-Ala-Gln(Trt)-Asp(OtBu)-Phe-Val-Gln(Trt)-Trp(Boc)-Leu-Met-Asn(Trt)Thr(t-Bu)-Gly-Gly-Pro-Ser(t-Bu)-Ser(t-Bu)-Gly-Ala-Pro-Pro-Pro-Ser(t-Bu)-rink amide resin. Subsequently, the resin was fully washed with N,N-dimethylformamide (DMF), dichloromethane (DCM), Methanol, dichloromethane (DCM), N,N-dimethylformamide (DMF) in sequence for three times respectively.

Thereto was added an N,N-dimethylformamide (DMF) mixed coupling solution (5 times excess of each) of FmocNH-PEG$_2$-OH (Quanta BioDesign), 2-(7-azo BTA)-N,N,N',N'-tetramethyluronium hexafluorophosphate (HATU) and diisopropylethyl amine (DIEPA), shaken for 2 hours, and filtrated. Subsequently, the resin was fully washed with N,N-dimethylformamide (DMF), dichloromethane (DCM), methanol, dichloromethane (DCM), and N,N-dimethylformamide (DMF) in sequence for three times respectively to obtain:

Boc-His(Boc)-D-Ser(t-Bu)-Gln(OtBu)-Gly-Thr(t-Bu)-Phe-Thr(t-Bu)-Ser(tBu)-Asp(OtBu)-Tyr(t-Bu)-Ser(t-Bu)-Lys(B oc)-Tyr(t-Bu)-Leu-Asp(OtBu)-Lys(Fmoc-PEG$_2$)-Arg(Pbf)-Arg(Pbf)-Ala-Gln(Trt)-Asp(OtBu)-Phe-Val-Gln(Trt)-Trp(Boc)-Leu-Met-Asn(Trt)-Thr(t-Bu)-Gly-Gly-Pro-Ser(t-Bu)-Ser(t-Bu)-Gly-Ala-Pro-Pro-Pro-Ser(t-Bu)-rink amide resin. Subsequently, the resin was fully washed with N,N-dimethylformamide (DMF), dichloromethane (DCM), methanol, dichloromethane (DCM), N,N-dimethylformamide (DMF) in sequence for three times respectively.

20% piperidine/N,N-dimethylformamide (DMF) solution was used to remove the Fmoc group (30 minutes, repeated removal for twice). Thereto was added an N,N-dimethylformamide (DMF) mixed coupling solution (5 times excess of each) of Fmoc-PEG$_2$-OH, 2-(7-azo BTA)-N,N,N',N'-tetramethyluronium hexafluorophosphate (HATU) and diisopropylethyl amine (DIEPA) to carry out the coupling reaction to obtain:

Boc-His(Boc)-D-Ser(t-Bu)-Gln(OtBu)-Gly-Thr(t-Bu)-Phe-Thr(t-Bu)-Ser(tBu)-Asp(OtBu)-Tyr(t-Bu)-Ser(t-Bu)-Lys(Boc)-Tyr(t-Bu)-Leu-Asp(OtBu)-Lys(Fmoc-PEG$_2$-PEG$_2$)-Arg(Pbf)-Arg(Pbf)-Ala-Gln(Trt)-Asp(OtBu)-Phe-Val-Gln(Trt)-Trp(Boc)-Leu-Met-Asn(Trt)-Thr(t-Bu)-Gly-Gly-Pro- Ser(t-Bu)-Ser(t-Bu)-Gly-Ala-Pro-Pro-Pro-Ser(t-Bu)-rink amide resin. The resin was fully washed with N,N-dimethylformamide (DMF), dichloromethane (DCM), methanol, dichloromethane (DCM), N,N-dimethylformamide (DMF) in sequence for three times respectively.

20% Piperidine/N,N-dimethylformamide (DMF) solution was used to remove the Fmoc group (30 minutes, repeated removal for twice). Fmoc-γGlu-OtBu was coupled according to conventional conditions in sequence and palmitic acid was added to obtain:

Boc-His(Boc)-D-Ser(t-Bu)-Gln(OtBu)-Gly-Thr(t-Bu)-Phe-Thr(t-Bu)-Ser(tBus)-Asp(OtBu)-Tyr(t-Bu)-Ser(t-Bu)-Lys(Boc)-Tyr(t-Bu)-Leu-Asp(OtBu)-Lys(PEG$_2$-PEG$_2$-C16)-Arg(Pbf)-Arg(Pbf)-Ala-Gln(Trt)-Asp(OtBu)-Phe-Val-Gln(Trt)-Trp(Boc)-Leu-Met-Asn(Trt)-Thr(t-Bu)-Gly-Gly-Pro-Ser(t-Bu)-Ser(t-Bu)-Gly-Ala-Pro-Pro-Pro-Ser(t-Bu)-rink amide resin. The resin was fully washed with N,N- dimethylformamide (DMF), dichloromethane (DCM), methanol and dichloromethane (DCM) in sequence for three times respectively, and dried under vacuum.

c) Removal of Polypeptide Full Protection:

Boc-His(Boc)-D-Ser(t-Bu)-Gln(OtBu)-Gly-Thr(t-Bu)-Phe-Thr(t-Bu)-Ser(tBu)-Asp(OtBu)-Tyr(t-Bu)-Ser(t-Bu)-Lys(Boc)-Tyr(t-Bu)-Leu-Asp(OtBu)-Lys(PEG$_2$-PEG$_2$-C16)-Arg(Pbf)-Arg(Pbf)-Ala-Gln(Trt)-Asp(OtBu)-Phe-Val-Gln(Trt)-Trp(Boc)-Leu-Met-Asn(Trt)-Thr(t-Bu)-Gly-Gly-Pro-Ser(t-Bu)-Ser(t-Bu)-Gly-Ala-Pro-Pro-Pro-Ser(t-Bu)-rink amide resin was added with a cutting fluid TFA/Phenol/thioanisole/EDT/H$_2$O (82.5:5:5:2.5:5, volume ratio) and heated, controlling the temperature of lysate at 25° C., and reacted for 2.5 hours. After filtration, the filter cake was washed with a small amount of lysate for three times, and the filtrates were combined. The filtrate was slowly poured into ice diethyl ether with stirring, placed on standing for more than 2 hours to precipitate completely. The precipitate was centrifuged and washed with ice diethyl ether for three times to obtain crude compound (SEQ ID NO: 6):

His-(D-Ser)-Gln-Gly-Thr-Phe-Thr-Ser-Asp-Tyr-Ser-Lys-Tyr-Leu-Asp-Lys(PEG$_2$-PEG$_2$-γGlu-CO(CH$_2$)$_{14}$CH$_3$)-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ d) Purification of Polypeptide Compound:

The resulting crude product was dissolved in a solution of acetonitrile (ACN):H$_2$O=1:2 (volume ratio), and purified by preparative HPLC on a 5.0 mm reverse-phase C18-packed 46 mm×250 mm column. 30% acetonitrile (containing 0.05% trifluoroacetic acid)/H$_2$O (containing 0.05% trifluoroacetic acid) were taken as starting materials to elute the column at a gradient (the proportion of acetonitrile is added at a speed of 1.33%/min) and a flow rate of 15 mL/min for 30 minutes, collect the components containing peptide, and lyophilize it so as to obtain a pure product with HPLC purity greater than 95%. The isolated product was analyzed by LC-MS.

Based on the above synthetic steps, the polypeptide compounds synthesized in the invention comprise (Table 1):

TABLE 1

Structure of polypeptide compounds synthesized in the examples of the invention

| Polypeptide (SEQ ID NO.) | Sequence | Theoretical Mass | Observed Mass |
|---|---|---|---|
| 1 | His-(D-Ser)-Gln-Gly-Thr-Phe-Thr-Ser-Asp-Tyr-Ser-Lys(PEG$_2$-PEG$_2$-γGlu-CO(CH$_2$)$_{14}$CH$_3$)-Lys-Leu-Asp-Aib-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ | 5019.5 | 5020.6 |
| 2 | His-(D-Ser)-Gln-Gly-Thr-Phe-Thr-Ser-Asp-Tyr-Ser-Lys(PEG$_2$-PEG$_2$-CO(CH$_2$)$_{16}$CO$_2$H)-Lys-Leu-Asp-Aib-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ | 4948.5 | 4949.6 |
| 3 | His-(D-Ser)-Gln-Gly-Thr-Phe-Thr-Ser-Asp-Tyr-Ser-Lys(PEG$_2$-PEG$_2$-CO(CH$_2$)$_{16}$CH$_3$)-Lys-Leu-Asp-Aib-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ | 4918.5 | 4920.1 |
| 4 | His-(D-Ser)-Gln-Gly-Thr-Phe-Thr-Ser-Asp-Lys(PEG$_2$-PEG$_2$-γGlu-CO(CH$_2$)$_{14}$CH$_3$)-Ser-Lys-Tyr-Leu-Asp-Aib-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ | 5019.5 | 5020.6 |
| 5 | His-(D-Ser)-Gln-Gly-Thr-Phe-Thr-Ser-Asp-Lys(PEG$_2$-PEG$_2$-γGlu-CO(CH$_2$)$_{16}$CO$_2$H)-Ser-Lys-Tyr-Leu-Asp-Aib-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ | 5077.6 | 5078.5 |
| 6 | His-(D-Ser)-Gln-Gly-Thr-Phe-Thr-Ser-Asp-Tyr-Ser-Lys-Tyr-Leu-Asp-Lys(PEG$_2$-PEG$_2$-γGlu-CO(CH$_2$)$_{14}$CH$_3$)-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ | 5097.6 | 5098.4 |
| 7 | His-(D-Ser)-Gln-Gly-Thr-Phe-Thr-Ser-Asp-Tyr-Ser-Lys-Tyr-Leu-Asp-Aib-Lys(PEG$_2$-PEG$_2$-γGlu-CO(CH$_2$)$_{16}$CO$_2$H)-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ | 5084.5 | 5085.6 |
| 8 | His-Aib-Gln-Gly-Thr-Phe-Thr-Ser-Asp-Lys(PEG$_2$-PEG$_2$-γGlu-CO(CH$_2$)$_{14}$CH$_3$)-Ser-Lys-Tyr-Leu-Asp-Aib-Arg-Arg-Ala-Gln-Asp-Phe-Val-Gln-Trp-Leu-Leu-Asp-Gly-Gly-Pro-Ser-Ser-Gly-Ala-Pro-Pro-Pro-Ser-NH$_2$ | 4901.8 | 4903.3 |

TABLE 1-continued

Structure of polypeptide compounds synthesized in the examples of the invention

| Polypeptide (SEQ ID NO.) | Sequence | Theoretical Mass | Observed Mass |
|---|---|---|---|
| 9 | His-(D-Ser)-Gln-Gly-Thr-Phe-Thr-Ser-Asp-Tyr-Ser-Lys(PEG$_2$-PEG$_2$-CO(CH$_2$)$_{14}$CH$_3$)-Lys-Leu-Asp-Aib-Arg-Arg-Ala-Gln-Asp-Phe-Val-Gln-Trp-Met-Asn-Thr-Gly-Gly-Pro-Ser-Ser-Gly-Ala-Pro-Pro-Pro-Ser-NH$_2$ | 4890.5 | 4891.6 |
| 10 | His-(D-Ser)-Gln-Gly-Thr-Phe-Thr-Ser-Asp-Tyr-Ser-Lys-Tyr-Leu-Asp-Aib-Lys(PEG$_2$-PEG$_2$-CO(CH$_2$)$_{16}$CO$_2$H)-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ | 4955.5 | 4956.6 |
| 11 | His-Aib-Gln-Gly-Thr-Phe-Thr-Ser-Asp-Lys(PEG$_2$-PEG$_2$-γGlu-CO(CH$_2$)$_{14}$CO$_2$H)-Ser-Lys-Tyr-Leu-Asp-Aib-Arg-Arg-Ala-Gln-Asp-Phe-Val-Gln-Trp-Leu-Leu-Asp-Gly-Gly-Pro-Ser-Ser-Gly-Ala-Pro-Pro-Pro-Ser-NH$_2$ | 4930.9 | 4928.8 |
| 12 | His-Aib-Gln-Gly-Thr-Phe-Thr-Ser-Asp-Lys(PEG$_2$-PEG$_2$-γGlu-CO(CH$_2$)$_{16}$CH$_3$)-Ser-Lys-Tyr-Leu-Asp-Aib-Arg-Arg-Ala-Gln-Asp-Phe-Val-Gln-Trp-Leu-Leu-Asp-Gly-Gly-Pro-Ser-Ser-Gly-Ala-Pro-Pro-Pro-Ser-NH$_2$ | 4928.9 | 4930.1 |
| 13 | His-Aib-Gln-Gly-Thr-Phe-Thr-Ser-Asp-Lys(PEG$_2$-PEG$_2$-γGlu-CO(CH$_2$)$_{14}$CO$_2$H)-Ser-Lys-Tyr-Leu-Asp-Glu-Arg-Arg-Ala-Gln-Asp-Phe-Val-Gln-Trp-Leu-Leu-Asp-Gly-Gly-Pro-Ser-Ser-Gly-Ala-Pro-Pro-Pro-Ser-NH$_2$ | 4974.6 | 4972.8 |
| 14 | His-Aib-Gln-Gly-Thr-Phe-Thr-Ser-Asp-Lys(PEG$_2$-PEG$_2$-γGlu-CO(CH$_2$)$_{16}$CH$_3$)-Ser-Lys-Tyr-Leu-Asp-Glu-Arg-Arg-Ala-Gln-Asp-Phe-Val-Gln-Trp-Leu-Leu-Asp-Gly-Gly-Pro-Ser-Ser-Gly-Ala-Pro-Pro-Pro-Ser-NH$_2$ | 4972.6 | 4971.2 |
| 15 | His-Aib-Gln-Gly-Thr-Phe-Thr-Ser-Asp-Lys(PEG$_2$-PEG$_2$-γGlu-CO(CH$_2$)$_{16}$CO$_2$H)-Ser-Lys-Tyr-Leu-Asp-Glu-Arg-Arg-Ala-Gln-Asp-Phe-Val-Gln-Trp-Leu-Leu-Asp-Gly-Gly-Pro-Ser-Ser-Gly-Ala-Pro-Pro-Pro-Ser-NH$_2$ | 5002.6 | 5003.8 |
| 16 | His-Aib-Gln-Gly-Thr-Phe-Thr-Ser-Asp-Lys(PEG$_2$-PEG$_2$-γGlu-CO(CH$_2$)$_{14}$CH$_3$)-Ser-Lys-Tyr-Leu-Asp-Glu-Arg-Arg-Ala-Gln-Asp-Phe-Val-Gln-Trp-Leu-Leu-Asp-Gly-Gly-Pro-Ser-Ser-Gly-Ala-Pro-Pro-Pro-Ser-NH$_2$ | 4945.5 | 4946.9 |
| 17 | His-(D-Ser)-Gln-Gly-Thr-Phe-Thr-Ser-Asp-Tyr-Ser-Lys-Tyr-Leu-Asp-Ser-Lys(PEG$_2$-PEG$_2$-γGlu-CO(CH$_2$)$_{16}$CO$_2$H)-Ala-Ala-His-Asp-Phe-Val-Glu-Trp-Leu-Leu-Arg-Ala-NH$_2$ | 4114.1 | 4116.0 |
| 18 | His-(D-Ser)-Gln-Gly-Thr-Phe-Thr-Ser-Asp-Tyr-Ser-Lys-Tyr-Leu-Asp-Glu-Lys-Ala-Ala-Lys(PEG$_2$-PEG$_2$-γGlu-CO(CH$_2$)$_{16}$CO$_2$H)-Glu-Phe-Ile-Glu-Trp-Leu-Leu-Arg-Ala-NH$_2$ | 4175.2 | 4176.9 |
| 19 | His-Aib-Gln-Gly-Thr-Phe-Thr-Ser-Asp-Lys(PEG$_2$-PEG$_2$-γGlu-CO(CH$_2$)$_{16}$CO$_2$H)-Ser-Lys-Tyr-Leu-Asp-Aib-Arg-Arg-Ala-Gln-Asp-Phe-Val-Gln-Trp-Leu-Leu-Asp-Gly-Gly-Pro-Ser-Ser-Gly-Ala-Pro-Pro-Pro-Ser-NH$_2$ | 4958.9 | 4960.3 |
| 20 | His-(D-Ser)-Gln-Gly-Thr-Phe-Thr-Ser-Asp-Tyr-Ser-Lys(PEG$_2$-PEG$_2$-γGlu-CO(CH$_2$)$_{16}$CO$_2$H)-Lys-Leu-Asp-Aib-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ | 5077.6 | 5078.3 |

TABLE 1-continued

Structure of polypeptide compounds synthesized in the examples of the invention

| Polypeptide (SEQ ID NO.) | Sequence | Theoretical Mass | Observed Mass |
|---|---|---|---|
| 21 | His-(D-Ser)-Gln-Gly-Thr-Phe-Thr-Ser-Asp-Tyr-Ser-Lys-Tyr-Leu-Asp-Ser-Lys(PEG$_2$-PEG$_2$-γGlu-CO(CH$_2$)$_{16}$CO$_2$H)-Ala-Ala-His-Asp-Phe-Val-Glu-Trp-Leu-Leu-Asn-Gly-Gly-Pro-Ser-Gly-Ala-Pro-Pro-Pro-Ser-NH$_2$ | 4892.4 | 4894.8 |
| 22 | His-(D-Ser)-Gln-Gly-Thr-Phe-Thr-Ser-Asp-Tyr-Ser-Lys-Tyr-Leu-Asp-Ser-Lys(PEG$_2$-PEG$_2$-γGlu-CO(CH$_2$)$_{16}$CH$_3$)-Ala-Ala-His-Asp-Phe-Val-Glu-Trp-Leu-Leu-Asn-Gly-Gly-Pro-Ser-Ser-Gly-Ala-Pro-Pro-Pro-Ser-NH$_2$ | 4862.4 | 4862.9 |
| 23 | His-(D-Ser)-Gln-Gly-Thr-Phe-Thr-Ser-Asp-Tyr-Ser-Lys-Tyr-Leu-Asp-Glu-Lys-Ala-Ala-Lys(PEG$_2$-PEG$_2$-γGlu-CO(CH$_2$)$_{14}$CH$_3$)-Glu-Phe-Ile-Glu-Trp-Leu-Leu-Arg-Ala-NH$_2$ | 4117.2 | 4117.8 |
| 24 | His-(D-Ser)-Gln-Gly-Thr-Phe-Thr-Ser-Asp-Tyr-Ser-Lys-Tyr-Leu-Asp-Glu-Lys-Ala-Ala-Lys(PEG$_2$-PEG$_2$-γGlu-CO(CH$_2$)$_{16}$CH$_3$)-Glu-Phe-Ile-Glu-Trp-Leu-Leu-Arg-Ala-NH$_2$ | 4145.2 | 4145.5 |
| 25 | His-(D-Ser)-Gln-Gly-Thr-Phe-Thr-Ser-Asp-Tyr-Ser-Lys-Tyr-Leu-Asp-Ser-Lys(PEG$_2$-PEG$_2$-γGlu-CO(CH$_2$)$_{16}$CH$_3$)-Ala-Ala-His-Asp-Phe-Val-Glu-Trp-Leu-Leu-Arg-Ala-NH$_2$ | 4084.1 | 4086.6 |
| 26 | His-(D-Ser)-Gln-Gly-Thr-Phe-Thr-Ser-Asp-Tyr-Ser-Lys-Tyr-Leu-Asp-Glu-Lys-Ala-Ala-Lys(PEG$_2$-PEG$_2$-γGlu-CO(CH$_2$)$_{16}$CO$_2$H)-Glu-Phe-Ile-Glu-Trp-Leu-Leu-Asn-Gly-Gly-Pro-Ser-Ser-Gly-Ala-Pro-Pro-Pro-Ser-NH$_2$ | 4953.5 | 4955.1 |
| 27 | His-(D-Ser)-Gln-Gly-Thr-Phe-Thr-Ser-Asp-Tyr-Ser-Lys-Tyr-Leu-Asp-Glu-Lys-Ala-Ala-Lys(PEG$_2$-PEG$_2$-γGlu-CO(CH$_2$)$_{14}$CO$_2$H)-Glu-Phe-Ile-Glu-Trp-Leu-Leu-Asn-Gly-Gly-Pro-Ser-Ser-Gly-Ala-Pro-Pro-Pro-Ser-NH$_2$ | 4925.5 | 4926.3 |
| 28 | His-(D-Ser)-Gln-Gly-Thr-Phe-Thr-Ser-Asp-Tyr-Ser-Lys-Tyr-Leu-Asp-Glu-Lys-Ala-Ala-Lys(PEG$_2$-PEG$_2$-γGlu-CO(CH$_2$)$_{16}$CH$_3$)-Glu-Phe-Ile-Glu-Trp-Leu-Leu-Asn-Gly-Gly-Pro-Ser-Ser-Gly-Ala-Pro-Pro-Pro-Ser-NH$_2$ | 4923.5 | 4924.0 |
| 29 | His-(D-Ser)-Gln-Gly-Thr-Phe-Thr-Ser-Asp-Tyr-Ser-Lys-Tyr-Leu-Asp-Glu-Lys-Ala-Ala-Lys(PEG$_2$-PEG$_2$-γGlu-CO(CH$_2$)$_{14}$CH$_3$)-Glu-Phe-Ile-Glu-Trp-Leu-Leu-Asn-Gly-Gly-Pro-Ser-Ser-Gly-Ala-Pro-Pro-Pro-Ser-NH$_2$ | 4895.5 | 4895.9 |
| 30 | His-(D-Ser)-Gln-Gly-Thr-Phe-Thr-Ser-Asp-Lys(PEG2-PEG$_2$-CO(CH$_2$)$_{16}$CO$_2$H)-Ser-Lys-Tyr-Leu-Asp-Aib-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ | 4948.5 | 4949.6 |
| 31 | His-(D-Ser)-Gln-Gly-Thr-Phe-Thr-Ser-Asp-Lys(PEG$_2$-PEG$_2$-CO(CH$_2$)$_{14}$CH$_3$)-Ser-Lys-Tyr-Leu-Asp-Aib-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ | 4890.5 | 4891.5 |
| 32 | His-(D-Ser)-Gln-Gly-Thr-Phe-Thr-Ser-Asp-Lys(PEG2-PEG$_2$-CO(CH$_2$)$_{16}$CH$_3$)-Ser-Lys-Tyr-Leu-Asp-Aib-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ | 4922.2 | 4920.9 |
| 33 | His-(D-Ser)-Gln-Gly-Thr-Phe-Thr-Ser-Asp-Tyr-Ser-Lys-Tyr-Leu-Asp-Aib-Lys(PEG$_2$-PEG$_2$-γGlu-CO(CH$_2$)$_{14}$CH$_3$)-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ | 5026.5 | 5027.6 |

TABLE 1-continued

Structure of polypeptide compounds synthesized in the examples of the invention

| Polypeptide (SEQ ID NO.) | Sequence | Theoretical Mass | Observed Mass |
|---|---|---|---|
| 34 | His-(D-Ser)-Gln-Gly-Thr-Phe-Thr-Ser-Asp-Tyr-Ser-Lys-Tyr-Leu-Asp-Lys(PEG$_2$-PEG$_2$-γGlu-CO(CH$_2$)$_{16}$CO$_2$H)-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ | 5155.6 | 5156.8 |
| 35 | His-(D-Ser)-Gln-Gly-Thr-Phe-Thr-Ser-Asp-Tyr-Ser-Lys-Tyr-Leu-Asp-Lys(PEG$_2$-PEG$_2$-CO(CH$_2$)$_{16}$CO$_2$H)-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ | 5026.5 | 5027.6 |
| 36 | His-(D-Ser)-Gln-Gly-Thr-Phe-Thr-Ser-Asp-Tyr-Ser-Lys-Tyr-Leu-Asp-Lys(PEG$_2$-PEG$_2$-γGlu-CO(CH$_2$)$_{16}$CH$_3$)-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ | 5125.6 | 5126.2 |
| 37 | His-(D-Ser)-Gln-Gly-Thr-Phe-Thr-Ser-Asp-Tyr-Ser-Lys-Tyr-Leu-Asp-Lys(PEG$_2$-PEG$_2$-γGlu-CO(CH$_2$)$_{14}$CH$_3$)-Arg-Arg-Ala-Gln-Asp-Phe-Val-Gln-Trp-Leu-Nle-Asn-Thr-Gly-Gly-Pro-Ser-Ser-Gly-Ala-Pro-Pro-Pro-Ser-NH$_2$ | 5081.2 | 5081.6 |

Example 2

In Vitro Inhibition Effect of GLP-1R/GCGR Dual Target Agonist Polypeptides on Hepatic Fibrosis Hepatic stellate cell strain LX-2 was selected to study and observe the effect of different doses of test substances on the expression of LX-2 cell activation marker ζ-SMA.

Hepatic stellate cell LX-2 was laid on 35 mm cell culture plate, cultured with DMEM (high glucose)+10% FBS+1% double-antibody culture medium (Thermo Fisher), placed overnight when the cells grew to 70% convergence at 37° C. and under the condition of 5% $CO_2$, and treated with the above compounds 1-37 (dissolved in PBS) for 48 hours the next day morning to extract cell protein, carry out Western Blot, and take β-actin as internal reference and analyze the expression quantities of α-SMA and β-actin by a gray level of Image J 1.50i. PBS with the same volume as that in experimental group was added in negative control.

0.1 μM, 1 μM and 5 μM of compounds 2, 5, 16 and 19 were treated, and could be able to reduce the expression of α-SMA under all concentrations and had a certain relation between volume and effect; but the negative control had no effect on the expression of α-SMA (Table 2).

Table 2 shows the result of hepatic fibrosis in vitro inhibiting experiment of the selected compounds 1-37 of the invention with a concentration of 1 μM. The integrating gray level of α-SMA/β-actin in the negative control group was 100% to analyze the in vitro inhibition activity of hepatic fibrosis of tested polypeptide.

TABLE 2

Effect of compounds 1-37 on relative expression of cell activation marker α-SMA of hepatic stellate cell strain LX-2.

| Polypeptide (SEQ ID NO.) | Concentration (μM) | Relative expression of α-SMA (α-SMA/β-actin, %) |
|---|---|---|
| Negative control | 0 | 100 |
| 1 | 1 | 75.26 |
| 2 | 0.1 | 72.77 |
|  | 1 | 33.71 |
|  | 5 | 31.62 |
| 3 | 1 | 82.25 |
| 4 | 1 | 88.50 |
| 5 | 0.1 | 66.04 |
|  | 1 | 67.94 |
|  | 5 | 33.45 |
| 6 | 1 | 41.19 |
| 7 | 1 | 73.52 |
| 8 | 1 | 80.25 |
| 9 | 1 | 75.86 |
| 10 | 1 | 71.49 |
| 11 | 1 | 96.78 |
| 12 | 1 | 72.99 |
| 13 | 1 | 97.93 |
| 14 | 1 | 92.80 |
| 15 | 1 | 77.29 |
| 16 | 0.1 | 65.32 |
|  | 1 | 48.88 |
|  | 5 | 40.35 |
| 17 | 1 | 75.38 |
| 18 | 1 | 75.60 |
| 19 | 0.1 | 71.48 |
|  | 1 | 43.46 |
|  | 5 | 39.75 |
| 20 | 1 | 68.39 |
| 21 | 1 | 97.66 |

TABLE 2-continued

Effect of compounds 1-37 on relative expression of cell activation marker α-SMA of hepatic stellate cell strain LX-2.

| Polypeptide (SEQ ID NO.) | Concentration (μM) | Relative expression of α-SMA (α-SMA/β-actin, %) |
|---|---|---|
| 22 | 1 | 90.56 |
| 23 | 1 | 95.91 |
| 24 | 1 | 82.42 |
| 25 | 1 | 93.34 |
| 26 | 1 | 94.44 |
| 27 | 1 | 92.34 |
| 28 | 1 | 87.62 |
| 29 | 1 | 89.36 |
| 30 | 1 | 85.53 |
| 31 | 1 | 86.89 |
| 32 | 1 | 97.14 |
| 33 | 1 | 95.45 |
| 34 | 1 | 88.18 |
| 35 | 1 | 61.28 |
| 36 | 1 | 62.49 |
| 37 | 1 | 42.45 |

It can be seen from Table 2 that the dual target agonist polypeptide compounds 1-37 of the invention all indicate the expression of excellent in vitro inhibiting LX-2 cell activation marker α-SMA. Wherein, the compounds 2, 5, 6, 16, 19, 20, 35 and 36 can obviously reduce the effect of relative expression of α-SMA.

Example 3

Functions of GLP-1R/GCGR Dual Target Agonist Polypeptides to Improve and Treat CCl$_4$-Induced Hepatic Fibrosis in Mice 6-8-week-old C57 mice with body weight of 20-25 g at SPF level were provided by Guangdong Medical Laboratory Animal Center and tested by SPF level laboratory in Laboratory Animal Center of Guangdong Pharmaceutical University. C57 mice were divided into control group, hepatic fibrosis model group and treatment group, 8 mice for each group. A mouse was subject to intraperitoneal injection with 20% CCl$_4$ (2 mL/kg, diluted with olive oil at ratio of 1:4) twice a week for continuous 6 weeks to form a stable hepatic fibrosis animal model. For the treatment group, one of subcutaneous injection compounds 2, 6 and 22 with 500 μg/kg of body weight was used respectively once every two days for continuous 6 weeks. Olive oil with same volume and same frequency was administered for the control group and stopped until the end of 6-week experiment. After the end of the experiment, the mice were subject to anesthesia to collect serum and liver specimens. The liver was fixed with 10% formalin and embedded with paraffin.

Figure 2:
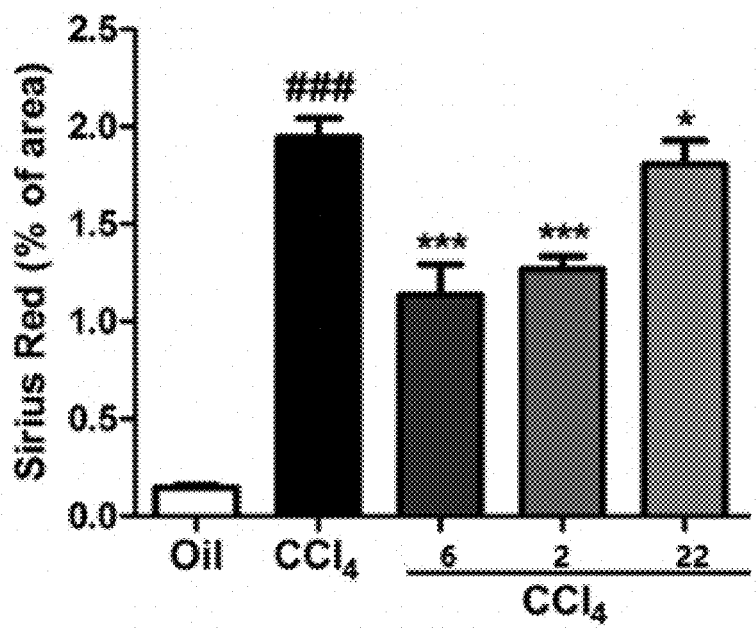
FIG. 2 is a diagram showing changes in the severity of hepatic fibrosis by Sirius red staining area, which are caused by the application of the compounds 2, 6 and 22 to CCl$_4$-induced hepatic fibrosis mice, (###: the severity of the group injected with CCl$_4$ significantly increases with the confidence level within 99.9% ($p<0.001$), compared with the control group only injected with olive oil; ***: the severity significantly decreases with the confidence level within 99.9% ($p<0.001$), compared with the control group injected with $CCl_4$); *: the severity significantly decreases with the confidence level within 95% ($p<0.05$), compared with the control group injected with $CCl_4$).
Figure 3:
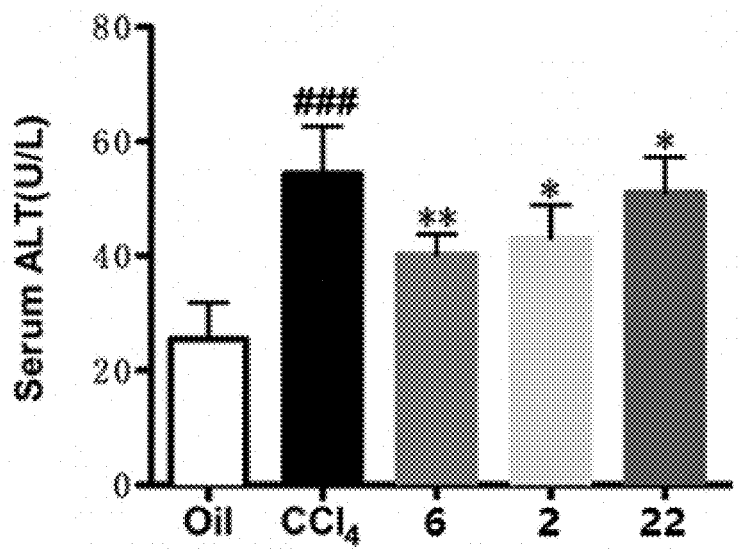
FIG. 3 is a diagram showing changes in the serum ALT, which are caused by the application of the compounds 2, 6 and 22 to $CCl_4$-induced hepatic fibrosis mice, (###: the serum ALT of the group injected with $CCl_4$ significantly increases with the confidence level within 99.9% ($p<0.001$), compared with the control group only injected with olive oil; **: the serum ALT significantly decreases with the confidence level within 99% ($p<0.01$), compared with the control group injected with $CCl_4$); *: the serum ALT significantly decreases with the confidence level within 95% ($p<0.05$), compared with the control group injected with $CCl_4$).

After induction of mice with CCl$_4$ for 6 weeks, the HE staining showed particularly obvious of hepatic cell injury and inflammatory infiltration in liver, and Sirius Red showed that obvious fibrosis nodules and pseudolobuli formed in liver (FIG. 1). The compounds 2, 6 and 22 obviously improved CCl$_4$-induced liver injury and fibrosis stage in mice (FIG. 1, FIG. 2). Simultaneously, the compounds 2, 6 and 22 could obviously reduce the ALT level of serum of mice with hepatic fibrosis (FIG. 3).

The results show that the compounds with different in vitro activities could obviously improve CCl$_4$-induced liver injury and fibrosis stage in mice, and obviously reduce the ALT level of serum of mice with hepatic fibrosis at the same time.

Example 4

Function of GLP-1R/GCGR Dual Target Agonist Polypeptides to Improve High Fat Diet-Induced NAFLD and Hyperlipemia 6-8-week-old C57 mice with body weight of 20-25 g at SPF level were provided by Guangdong Medical Laboratory Animal Center and tested by SPF level laboratory in Laboratory Animal Center of Guangdong Pharmaceutical University. C57 mice were divided into control group, hepatic fibrosis model group and treatment group, 8 mice for each group. The mice were fed with high fat diet (HFD) for 12 weeks. For the treatment group, subcutaneous injection compounds 2 and 6 with 500 μg/kg of body weight were used once every two days for continuous 12 weeks. PBS with same volume and same frequency was administered for the control group. After the end of the experiment, the mice were subject to anesthesia to collect serum and liver specimens.

Figure 4:
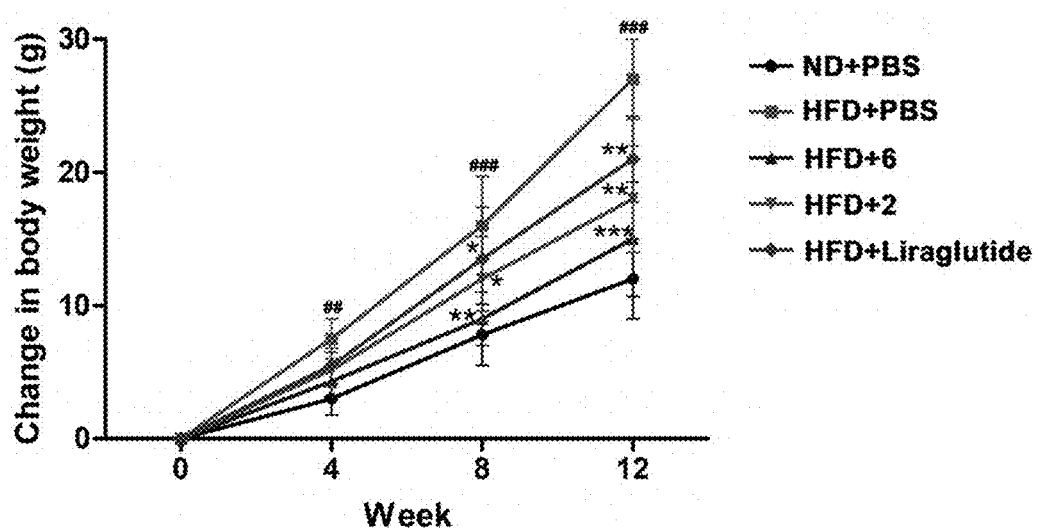
FIG. 4 is a diagram showing changes in the body weight, which are caused by the application of the compounds 2 and 6 or Liraglutide to high fat diet-induced hyperlipidemic mice (###: the body weight significantly increases with the confidence level within 99.9% ($p<0.001$), compared with the control group fed with normal diet; ##: the body weight significantly increases with the confidence level within 99% ($p<0.01$), compared with the control group fed with normal diet; *: the body weight significantly decreases with the confidence level within 99.9% ($p<0.001$), compared with the control group fed with high fat diet; : the body weight significantly decreases with the confidence level within 99% ($p<0.01$), compared with the control group fed with high fat diet; *: the body weight significantly decreases with the confidence level within 95% ($p<0.05$), compared with the control group fed with high fat diet).
Figure 5:
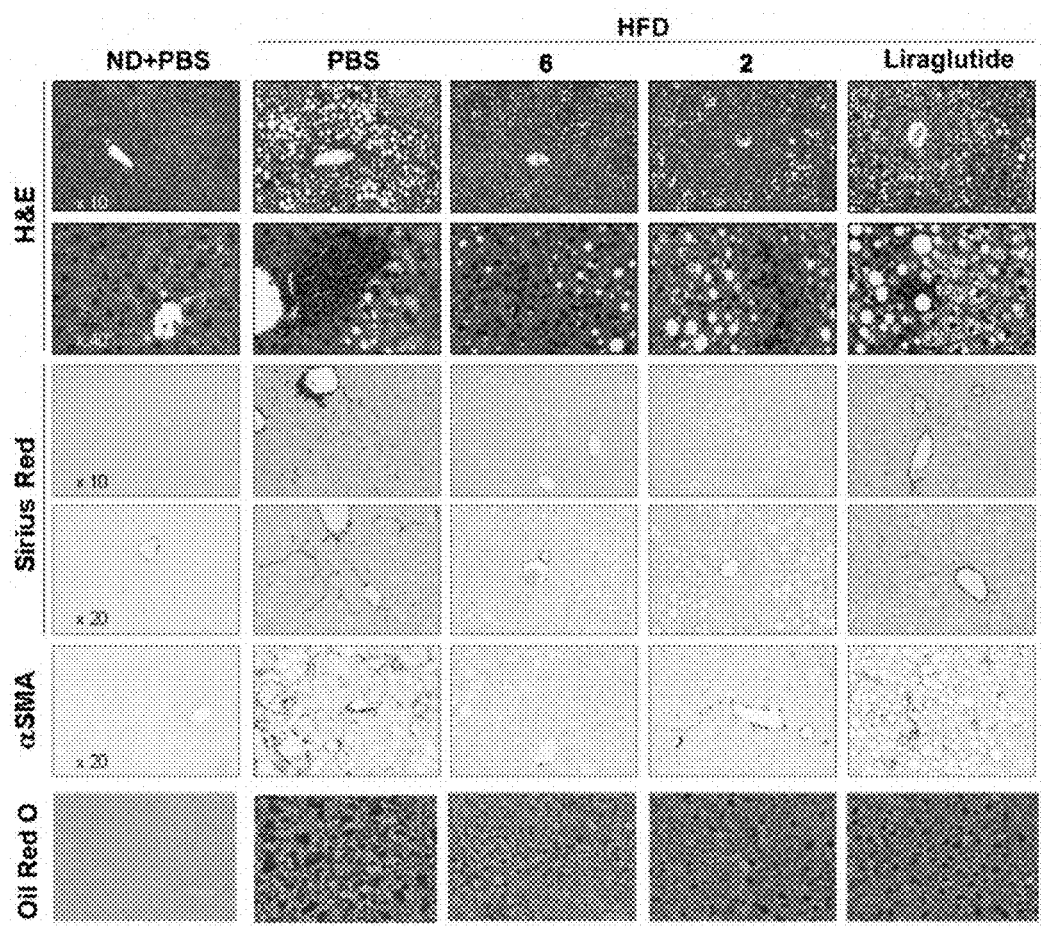
FIG. 5 shows the immunohistochemical staining results of hepatic tissue sections, which are caused by the application of the compounds 2 and 6 or Liraglutide to high fat diet-induced hyperlipidemic mice.
Figure 6:
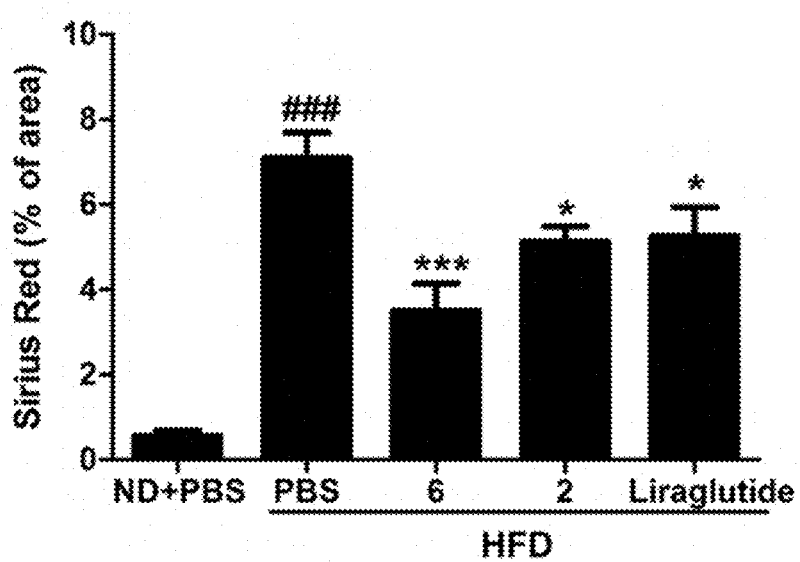
FIG. 6 is a diagram showing changes in the area of fibrosis nodule indicated by the Sirius red stain, which are caused by the application of the compounds 2 and 6 or Liraglutide to high fat diet-induced hyperlipidemic mice (###: the area significantly increases with the confidence level within 99.9% ($p<0.001$), compared with the control group fed with normal diet; ***: the area significantly decreases with the confidence level within 99.9% ($p<0.001$), compared with the control group fed with high fat diet; *: the area significantly decreases with the confidence level within 95% ($p<0.05$), compared with the control group fed with high fat diet).
Figure 7:
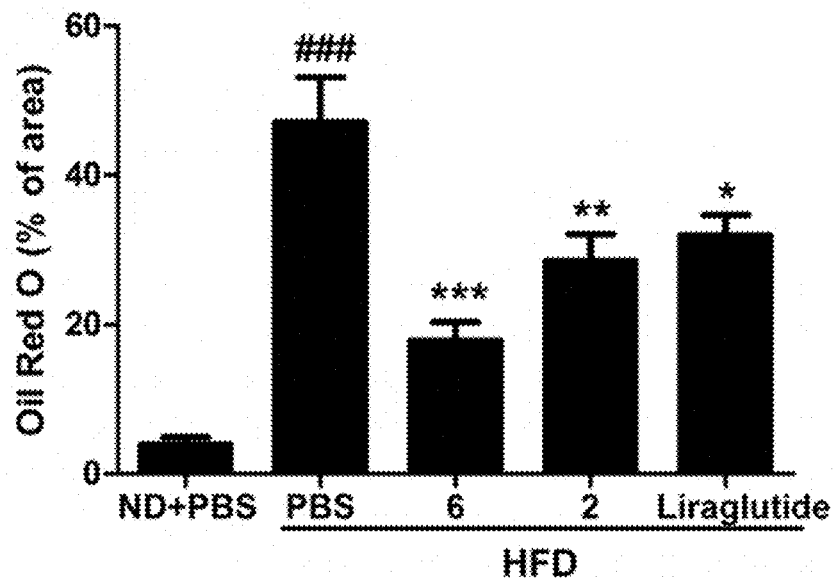
FIG. 7 is a diagram showing changes in the area of liver lipid deposition indicated by Oil Red O stain, which are caused by the application of the compounds 2 and 6 or Liraglutide to high fat diet-induced hyperlipidemic mice (###: the area significantly increases with the confidence level within 99.9% ($p<0.001$), compared with the control group fed with normal diet; *: the area significantly decreases with the confidence level within 99.9% ($p<0.001$), compared with the control group fed with high fat diet; : the area significantly decreases with the confidence level within 99% ($p<0.01$), compared with the control group fed with high fat diet; *: the area significantly decreases with the confidence level within 95% ($p<0.05$), compared with the control group fed with high fat diet).
Figure 8:
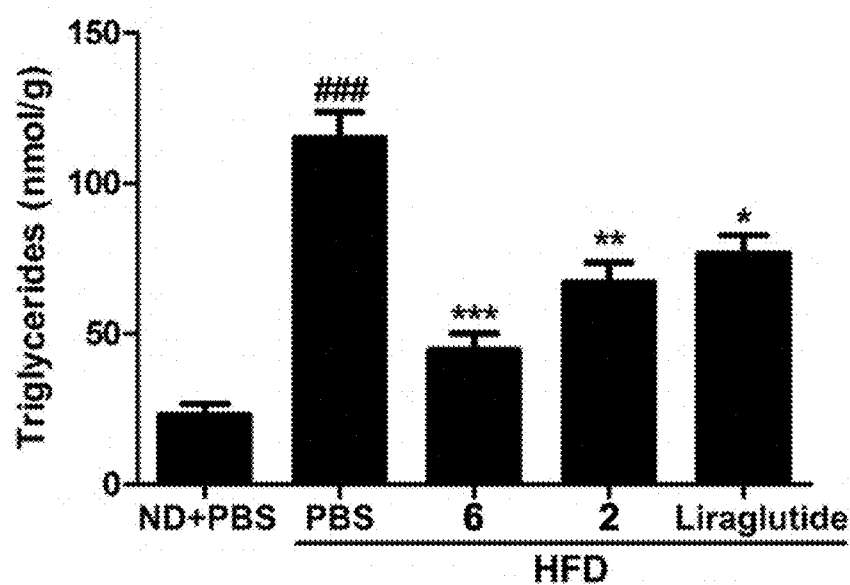
FIG. 8 is a diagram showing changes in the hepatic triglyceride (TG) caused by the application of the compounds 2 and 6 or Liraglutide to high fat diet-induced hyperlipidemic mice (###: the TG significantly increases with the confidence level within 99.9% ($p<0.001$), compared with the control group fed with normal diet; *: the TG significantly decreases with the confidence level within 99.9% ($p<0.001$), compared with the control group fed with high fat diet; : the TG significantly decreases with the confidence level within 99% ($p<0.01$), compared with the control group fed with high fat diet; *: the TG significantly decreases with the confidence level within 95% ($p<0.05$), compared with the control group fed with high fat diet).
Figure 9:
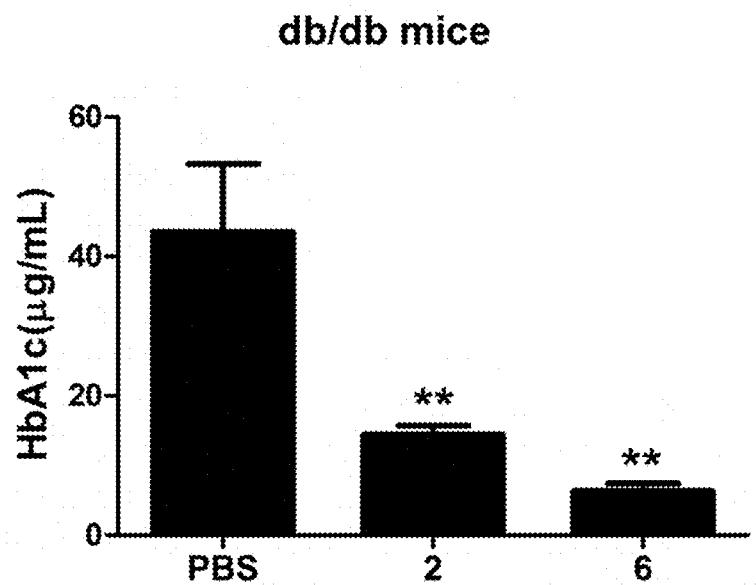
FIG. 9 is a diagram showing changes in the glycosylated hemoglobin (HbAlc) in serum caused by the application of the compounds 2 and 6 to db/db mice (**: the HbAlc significantly decreases with the confidence level within 99% ($p<0.01$), compared with the control group).
Figure 10:
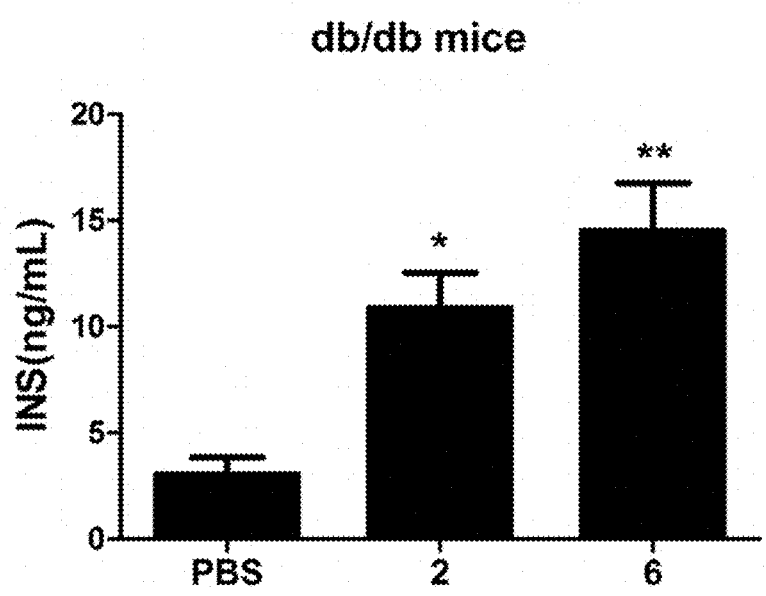
FIG. 10 is a diagram showing changes in the insulin (INS) in serum caused by the application of the compounds 2 and 6 to db/db mice (**: the INS significantly increases with the confidence level within 99% ($p<0.01$), compared with the control group; *: the INS significantly increases with the confidence level within 95% ($p<0.05$), compared with the control group).
Figure 11:
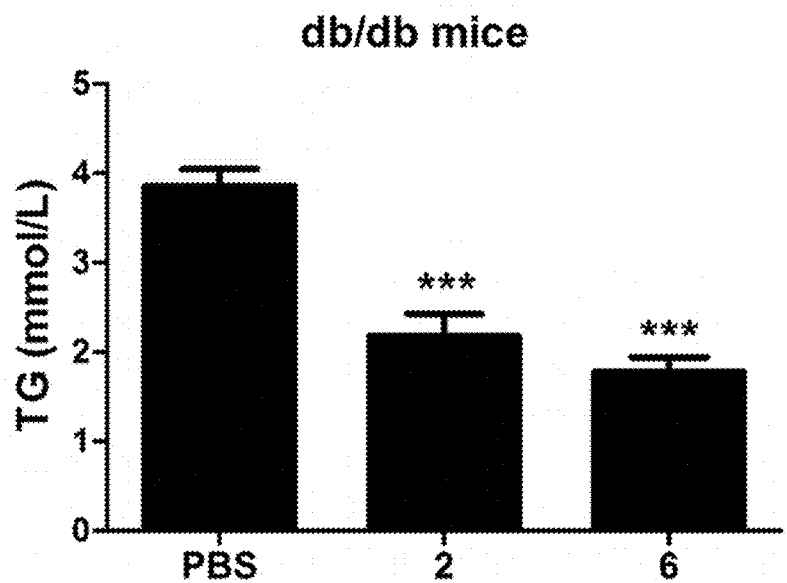
FIG. 11 is a diagram showing changes in the triglyceride (TG) in serum caused by the application of the compounds 2 and 6 to db/db mice (***: the TG significantly decreases with the confidence level within 99.9% ($p<0.001$), compared with the control group).
Figure 12:
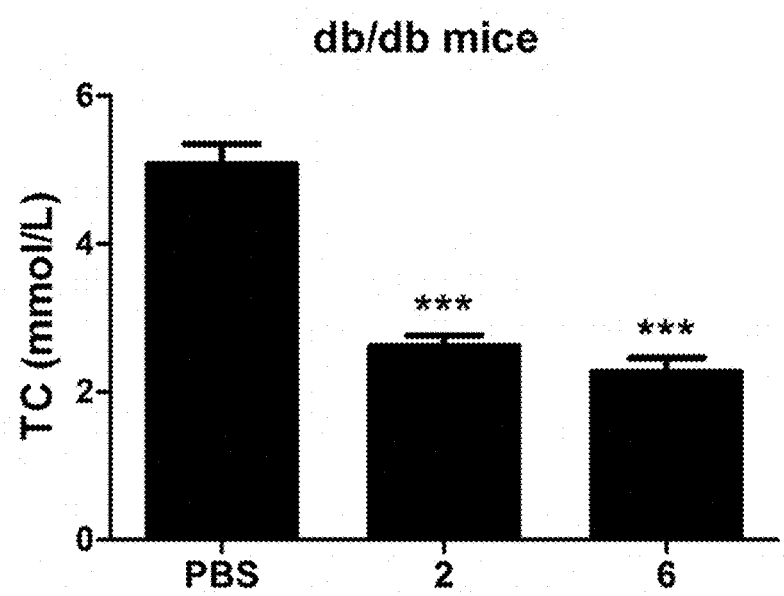
FIG. 12 is a diagram showing changes in the total cholesterol (TC) in serum caused by the application of the compounds 2 and 6 to db/db mice (***: the TC significantly decreases with the confidence level within 99.9% ($p<0.001$), compared with the control group).

The compounds 6 and 2 were able to effectively inhibit HFD-induced increase of body weight of mice, and the compound 6 could control the body weight most obviously. In addition, the control effect of the compound 2 on body weight was equivalent to that of liraglutide (FIG. 4). The liver tissue biopsy result showed that the compounds 6 and 2 were able to inhibit liver lipoid degeneration and non-alcoholic steatohepatitis, and effectively inhibit fatty liver complicated by hepatic fibrosis (FIG. 5 and FIG. 6). The compounds 6 and 2 were able to effectively reduce liver lipid deposition (FIG. 7) and hepatic triglyceride (TG) content (FIG. 8) in mice, and the treatment effect of compounds 6 and 2 were obviously better than Liraglutide. It was indicated that the compounds 6 and 2 had good in vivo activity for hepatic fibrosis and hyperlipidaemia complicated by non-alcoholic steatohepatitis.

The above results show that the compounds 6 and 2 as GLP-1R/GCGR dual target agonist had significant effect on preventing and treating high fat diet-induced NAFLD complicated by hepatic fibrosis in mice.

Example 5

Effect of GLP-1R/GCGR Dual Target Agonist Polypeptide on Glucolipid Metabolism of Diabetic Mice 12-week-old db/db diabetic obese mice were randomly grouped into 3 groups (12-hour fasting before grouping), 6 mice in each group. Mice in each group were injected subcutaneously at a dose of 10 μg/mouse, and mice in the blank group were injected subcutaneously with PBS. The volume for each group was 0.25 ml/mouse once every two days (at 48-hour interval) for 18 days. At the end of the experiment, blood was taken from the orbital venous plexus of each mouse to measure glycosylated hemoglobin (HbAlc), insulin (INS), triglyceride (TG) and total cholesterol (TC) levels in the serum of the mouse. The liver, pancreas, heart, lungs and spleen were taken for HE pathological staining at the same time. GraphPad Prismversion6 software was used for statistical analysis.

Compared with the blank group of diabetic mice, the compounds 2 and 6 significantly reduced the HbAlc level of the db/db diabetic mice and up-regulated the insulin level, indicating that the compounds 2 and 6 could reduce blood glucose by promoting the pancreas islet for insulin secretion. In addition, the compounds 2 and 6 could obviously inhibit the triglyceride (TG) and total cholesterol (TC) levels of the db/db diabetic mice, indicating that the compounds 2 and 6 had obvious lipid-lowering effect. And the effect of the glucolipid metabolism of the compound 6 was improved (FIG. 8-12).

Figure 13:
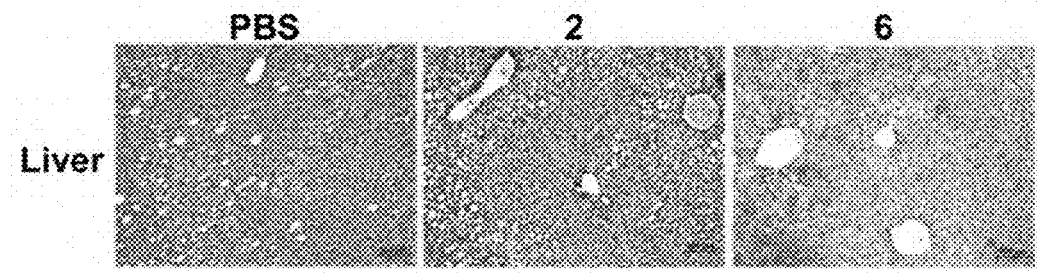
FIG. 13 is an immunohistochemical staining diagram of hepatic tissue sections, showing the changes in fatty vacuolar degeneration and adipositis in hepatic tissues caused by the application of the compounds 2 and 6 to db/db mice.

The tissue biopsy results show that lipoid vacuolar degeneration and lipid inflammation were obviously found in the liver of each diabetic mouse treated with blank PBS, and the compounds 2 and 6 could significantly inhibit liver lipoid vacuolar degeneration and lipid inflammation in diabetic mice, especially that the compound 6 had better inhibition effect (FIG. 13).

Figure 14:
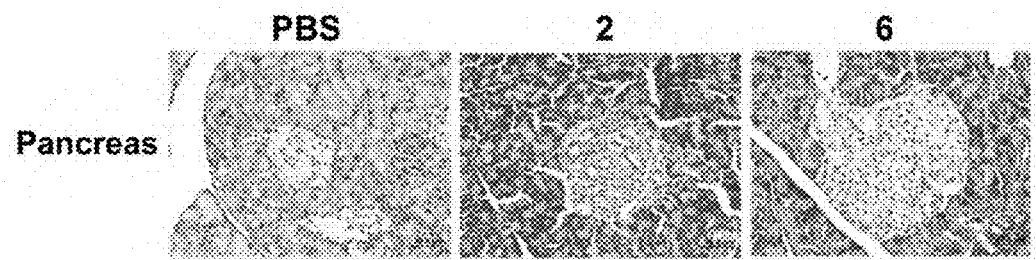
FIG. 14 is an immunohistochemical staining diagram of pancreatic tissue sections, showing the changes in pancreatic islet in pancreatic tissues caused by the application of the compounds 2 and 6 to db/db mice.

In addition, the pancreatic islets in pancreatic tissues of the blank diabetic mice were obviously atrophied, and the compounds 2 and 6 could significantly improve the atrophy lesions of islets in the diabetic mice (FIG. 14).

Figure 15:
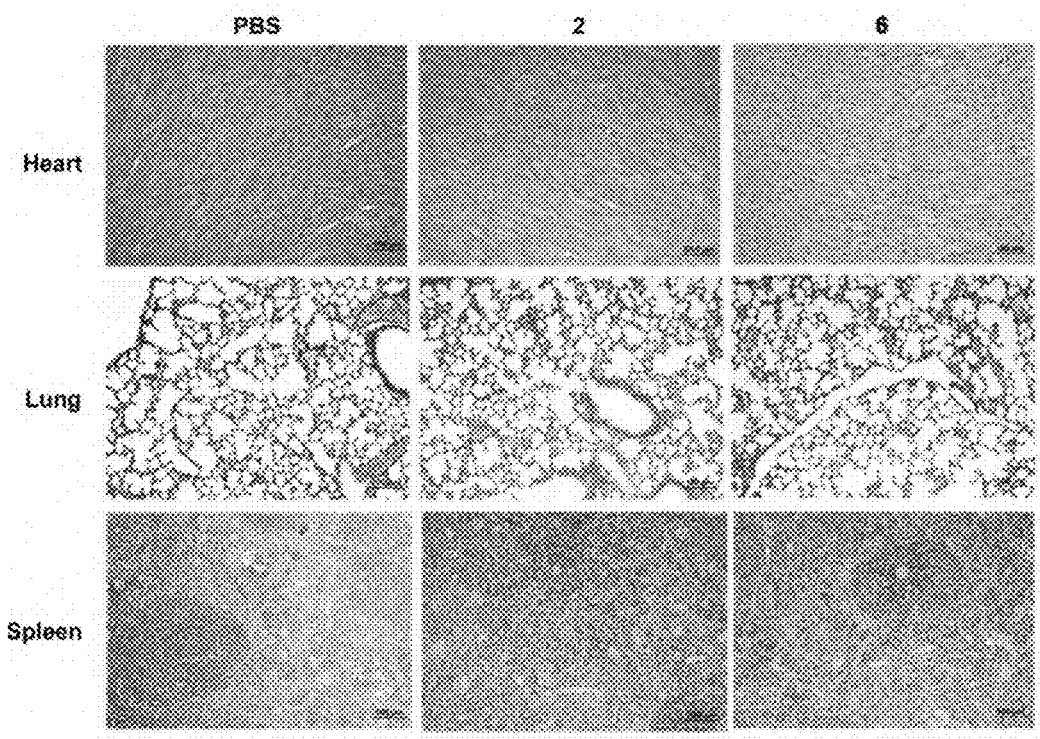
FIG. 15 is an immunohistochemical staining diagram of tissue sections of heart, lung and spleen, showing that no histological change in heart, lung and spleen is caused by the application of the compounds 2 and 6 to db/db mice.
Figure 16:
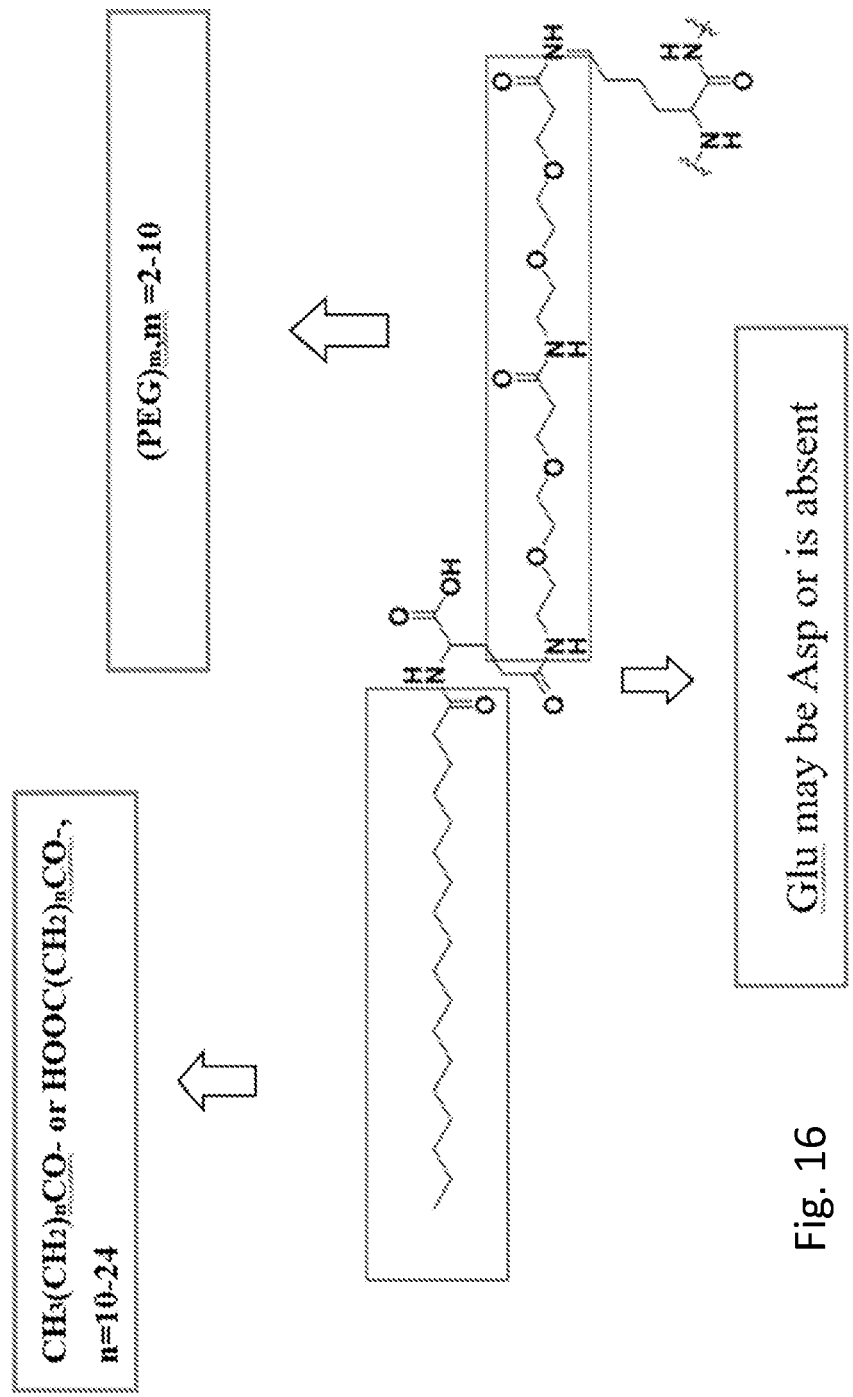
FIG. 16 illustrates that a bridging group may be Glu-(PEG)m or Asp-(PEG)m or (PEG)m.

FIG. 15 shows no obvious pathological changes in the hearts, lungs and spleens of the diabetic mice in the blank and administration groups, indicating that the compounds 2 and 6 had reliable safety during subcutaneous injection at therapeutic dose.

The examples are used to illustrate the invention. Although not indicated, all polypeptides can achieve the technical effect of the invention within the protection scope of the invention, and various changes and modifications may be made by those skilled in the art in accordance with the invention, without departing from the spirit of the invention, and are within the scope of the appended claims of the invention.

What is claimed is:

1. A method of preventing or treating non-alcoholic fatty liver diseases (NAFLDs), hyperlipemia, and/or arteriosclerosis in a subject, the method comprising:
administering to the subject at least one GLP-1R/GCGR dual target agonist polypeptide comprising a parent peptide represented by the following amino acid sequence: His-Xaa2-Gln-Gly-Thr-Phe-Thr-Ser-Asp-Xaa10-Ser-Lys-Xaa13-Leu-Asp-Xaa16-Xaa17-Xaa18-Ala-Xaa20-Xaa21-Phe-Xaa23-Xaa24-Trp-Leu-Xaa27-Xaa28-Xaa29-Xaa30-Xaa31-Xaa32-Xaa33-Xaa34-Xaa35-Xaa36-Xaa37-Xaa38-Xaa39-Xaa40-COR$_1$ (SEQ ID NO: 38)
wherein, R$_1$=—NH$_2$;
Xaa2=Aib, or D-Ser;
Xaa10=Lys or Tyr;
Xaa13=Lys or Tyr;
Xaa16=Aib, Lys or Glu;
Xaa17=Arg;
Xaa18=Arg;
Xaa20=Gln;
Xaa21=Asp;
Xaa23=Val;
Xaa24=Gln;
Xaa27=Met, Leu, or Nle;
Xaa28=Asp, or Asn;
Xaa29=Thr or is absent;
Xaa30=Gly;
Xaa31=Gly;
Xaa32=Pro;
Xaa33=Ser;
Xaa34=Ser;
Xaa35=Gly;
Xaa36=Ala;
Xaa37=Pro;
Xaa38=Pro;
Xaa39=Pro;
Xaa40=Ser;
in the amino acid sequence of the parent peptide, at least one of Xaa10, or Xaa16 is Lys, the side chain of the at least one Lys or the Lys at position 12 of the sequence is attached to a lipophilic substituent in such a way that a carboxyl group of the lipophilic substituent forms an amide bond with an amino of a bridging group, the bridging group is attached to the parent peptide by means of a carboxyl group of the amino acid residue of the bridging group which forms an amide bond with the amino group of the side chain of said at least one Lys or the Lys of the parent peptide, the bridging group is Glu-(PEG)$_m$ or Asp-(PEG)$_m$ or (PEG)$_m$, wherein m is an integer of 2-10; the lipophilic substituent is an acyl group selected from CH$_3$(CH$_2$)$_n$CO— or HOOC(CH$_2$)$_n$CO—, wherein n is an integer of 10-24.

2. The method according to claim 1, wherein a molecular bridge is formed by means of the bridging group between the side chains of amino acid residue pairs 12 and 16, 16 and 20, 17 and 21, or 20 and 24 in the amino acid sequence.

3. The method according to claim 1, wherein the Lys attached to the lipophilic substituent is replaced with Homo-Lys, Orn, Dap or Dab.

4. The method according to claim 1, wherein the parent peptide has an amino acid sequence of: His-Xaa2-Gln-Gly-Thr-Phe-Thr-Ser-Asp-Xaa10-Ser-Lys-Xaa13-Leu-Asp-Xaa16-Xaa17-Xaa18-Ala-Xaa20-Xaa21-Phe-Xaa23-Xaa24-Trp-Leu-Xaa27-Xaa28-Xaa29-Xaa30-Xaa31-Xaa32-Xaa33-Xaa34-Xaa35-Xaa36-Xaa37-Xaa38-Xaa39-Xaa40-COR$_1$ (SEQ ID NO: 38)
wherein, R$_1$=—NH$_2$;
Xaa2=D-Ser;
Xaa10=Tyr;
Xaa13=Tyr;
Xaa16=Lys;
Xaa17=Arg;
Xaa18=Arg;
Xaa20=Gln;
Xaa21=Asp;
Xaa23=Val;
Xaa24=Gln;
Xaa27=Met, Leu or Nle;
Xaa28=Asn;
Xaa29=Gly;
Xaa30=Gly;
Xaa31=Gly;
Xaa32=Pro;
Xaa33=Ser;
Xaa34=Ser;
Xaa35=Gly;
Xaa36=Ala;
Xaa37=Pro;
Xaa38=Pro;
Xaa39=Pro;
Xaa40=Ser.

5. The method according to claim 1, wherein when the position 10, 12, or 16 of the amino acid sequence is Lys, the lipophilic substituent attached to the side chain of the Lys is one of the following structures:

Lys(PEG$_2$-PEG$_2$—CO(CH$_2$)$_{14}$CH$_3$):
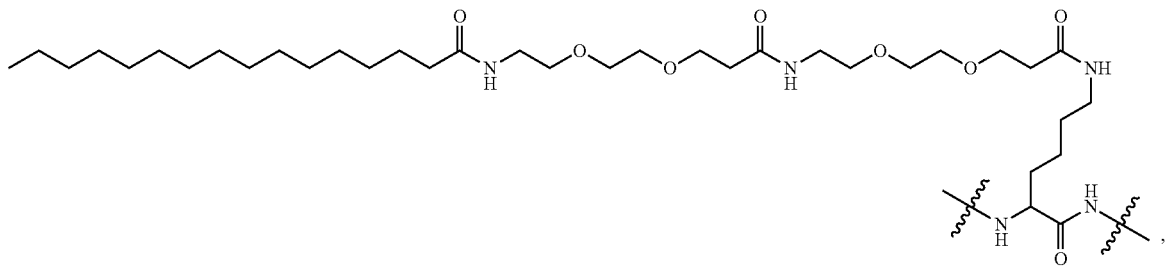
Lys(PEG$_2$-PEG$_2$-γGlu-CO(CH$_2$)$_{14}$CH$_3$):
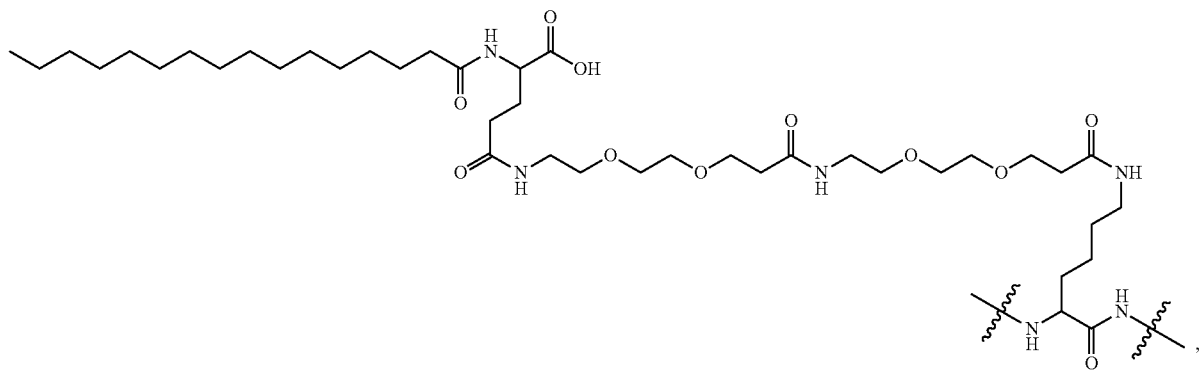
Lys(PEG$_2$-PEG$_2$—CO(CH$_2$)$_{14}$CO$_2$H):
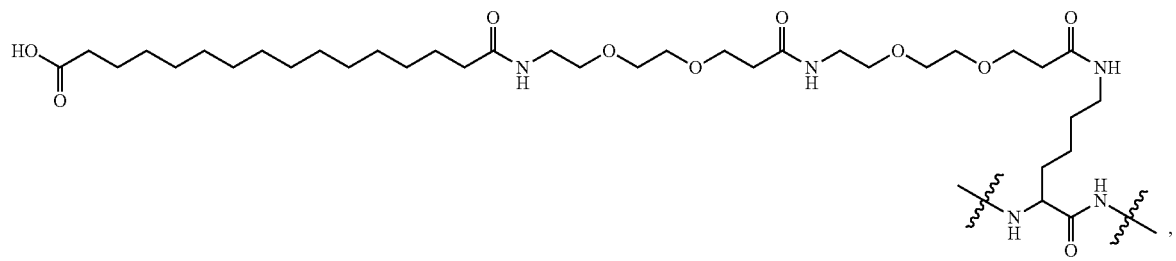
Lys(PEG$_2$-PEG$_2$-γGlu-CO(CH$_2$)$_{14}$CO$_2$H):
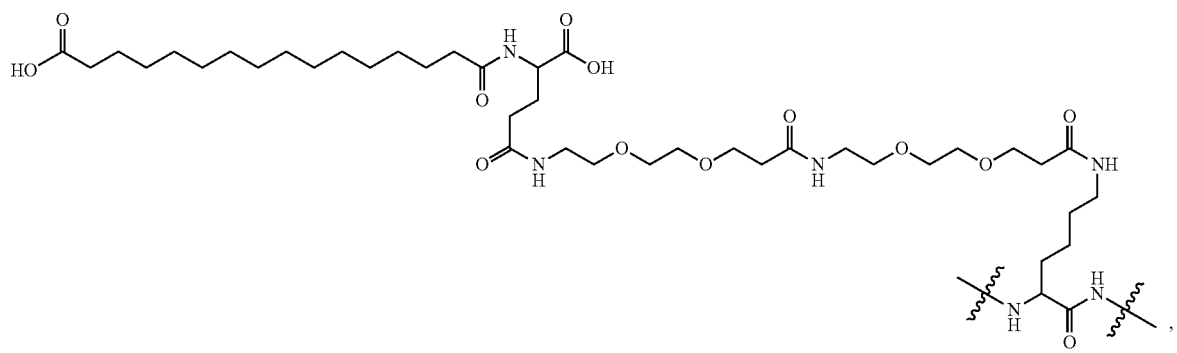
Lys(PEG$_2$-PEG$_2$—CO(CH$_2$)$_{16}$CO$_2$H):
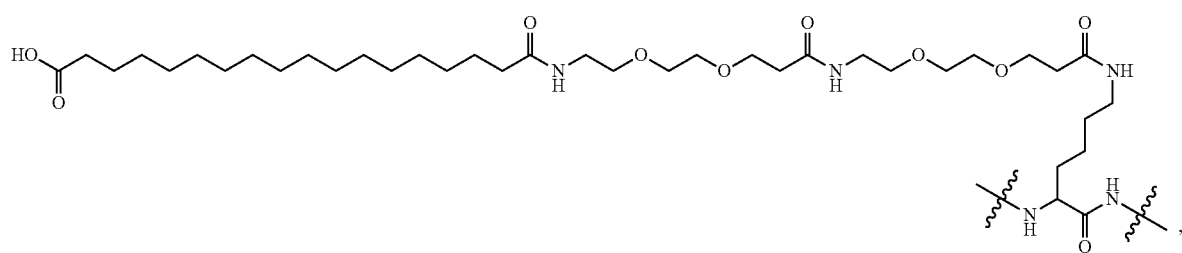

Lys(PEG₂-PEG₂-γGlu-CO(CH₂)₁₆CO₂H):

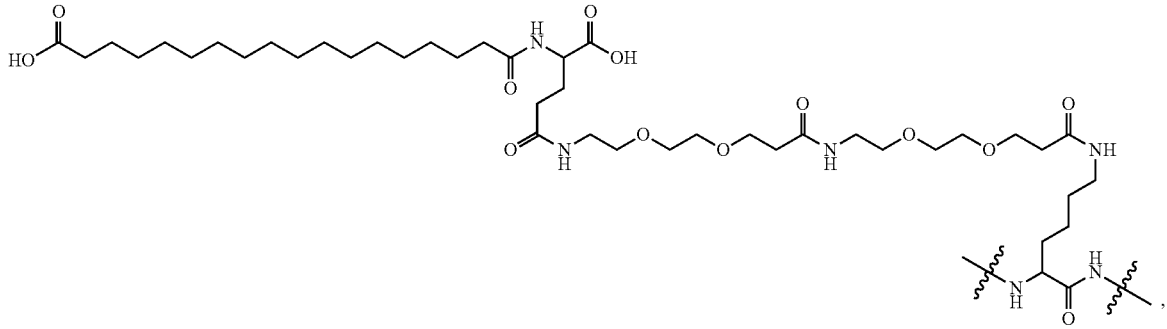

Lys(PEG₂-PEG₂—CO(CH₂)₁₆CH₃):

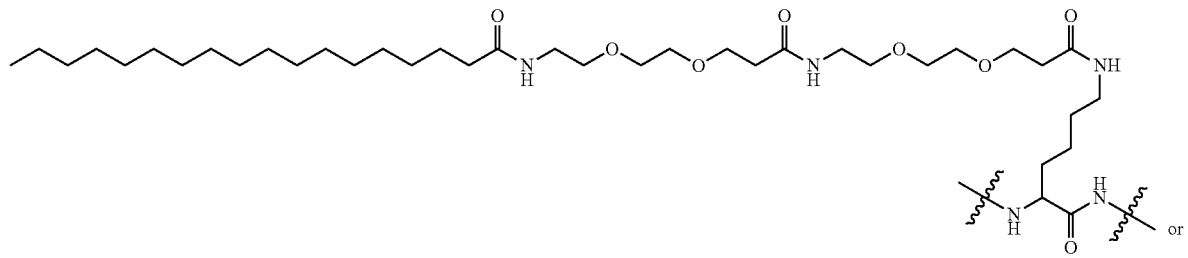

Lys(PEG₂-PEG₂-γGlu-CO(CH₂)₁₆CH₃):

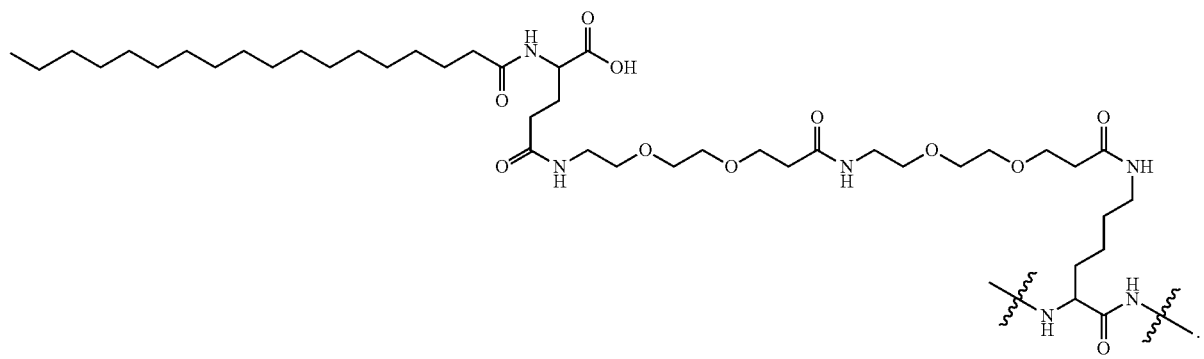

6. The method according to claim 1, wherein the amino acid sequence of the parent peptide is selected from the group consisting of SEQ ID NO:2, SEQ ID NO:5, SEQ ID NO:6, SEQ ID NO:16, SEQ ID NO:19, SEQ ID NO:20, SEQ ID NO:35, SEQ ID NO:36 and SEQ ID NO:37.

7. The method according to claim 1, wherein the NAFLDs comprise non-alcoholic lipoid degeneration, non-alcoholic steatohepatitis, hepatic fibrosis or liver cirrhosis complicated by hepatic fibrosis.

8. The method according to claim 1, wherein the administered GLP-1R/GCGR dual target agonist polypeptide compound is contained within a pharmaceutically acceptable carrier.

9. The method according to claim 1, wherein the GLP-1R/GCGR dual target agonist polypeptide compound is one as follows:

Compound 2 (SEQ ID NO: 2):
His-(D-Ser)-Gln-Gly-Thr-Phe-Thr-Ser-Asp-Thr-Ser-Lys(PEG₂-PEG₂-CO(CH₂)₁₆CO₂H)-Lys-Leu-Asp-Aib-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH₂;

Compound 5 (SEQ ID NO: 5):
His-(D-Ser)-Gln-Gly-Thr-Phe-Thr-Ser-Asp-Lys(PEG₂-PEG₂-γGlu-CO(CH₂)₁₆CO₂H)-Ser-Lys-Tyr-Leu-Asp-Aib-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH₂;

Compound 6 (SEQ ID NO: 6):
His-(D-Ser)-Gln-Gly-Thr-Phe-Thr-Ser-Asp-Tyr-Ser-Lys-Tyr-Leu-Asp-Lys(PEG₂-PEG₂-γGlu-COCO(CH₂)₁₄CH₃)-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH₂;

Compound 16 (SEQ ID NO: 16):
His-Aib-Gln-Gly-Thr-Phe-Thr-Ser-Asp-Lys(PEG₂-PEG₂-γGlu-CO(CH₂)₁₄CH₃)-Ser-Lys-Tyr-Leu-Asp-Glu-Arg-Arg-Ala-Gln-Asp-Phe-Vhl-Gln-Trp-Leu-Leu-Asp-Gly-Gly-Pro-Ser-Ser-Gly-Ala-Pro-Pro-Pro-Ser-NH₂;

Compound 19 (SEQ ID NO: 19):
His-Aib-Gln-Gly-Thr-Phe-Thr-Ser-Asp-Lys(PEG₂-PEG₂-γGlu-CO(CH₂)₁₆CO₂H)-Ser-Lys-Tyr-Leu-Asp-Aib-Arg-Arg-Ala-Gln-Asp-Phe-Val-Gln-Trp-Leu-Leu-Asp-Gly-Gly-Pro-Ser-Ser-Gly-Ala-Pro-Pro-Pro-Ser-NH₂;

Compound 20 (SEQ ID NO: 20):
His-(D-Ser)-Gln-Gly-Thr-Phe-Thr-Ser-Asp-Tyr-Ser-Lys(PEG₂-PEG₂-γGlu-CO(CH₂)₁₆CO₂H)-Lys-Leu-Asp- Aib-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$;

Compound 35 (SEQ ID NO: 35):

His-(D-Ser)-Gln-Gly-Thr-Phe-Thr-Ser-Asp-Tyr-Ser-Lys-Tyr-Leu-Asp-Lys(PEG$_2$-PEG$_2$-CO(CH$_2$)$_{16}$CO$_2$H)-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$;

Compound 36 (SEQ ID NO: 36):

His-(D-Ser)-Gln-Gly-Thr-Phe-Thr-Ser-Asp-Tyr-Ser-Lys-Tyr-Leu-Asp-Lys(PEG$_2$-PEG$_2$-$_\gamma$Glu-CO(CH$_2$)$_{16}$CH$_3$)-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$;

or

Compound 37 (SEQ ID NO: 37):

His-(D-Ser)-Gln-Gly-Thr-Phe-Thr-Ser-Asp-Tyr-Ser-Lys-Tyr-Leu-Asp-(PEG$_2$-PEG$_2$-$_\gamma$Glu-CO(CH$_2$)$_{14}$CH$_3$)-Arg-Arg-Ala-Gln-Asp-Phe-Val-Gln-Trp-Leu-Nle-Asn-Thr-Gly-Gly-Pro-Ser-Ser-Gly-Ala-Pro-Pro-Pro-Ser-NH$_2$.

\* \* \* \* \*

```
                          SEQUENCE LISTING

<160> NUMBER OF SEQ ID NOS: 38

<210> SEQ ID NO 1
<211> LENGTH: 40
<212> TYPE: PRT
<213> ORGANISM: Artificial
<220> FEATURE:
<223> OTHER INFORMATION: GLP-1R/GCGR dual target agonist polypeptide
<220> FEATURE:
<221> NAME/KEY: MISC_FEATURE
<222> LOCATION: (2)..(2)
<223> OTHER INFORMATION: D-Ser
<220> FEATURE:
<221> NAME/KEY: MISC_FEATURE
<222> LOCATION: (16)..(16)
<223> OTHER INFORMATION: X=Aib

<400> SEQUENCE: 1

His Ser Gln Gly Thr Phe Thr Ser Asp Tyr Ser Lys Lys Leu Asp Xaa
1               5                   10                  15

Arg Arg Ala Gln Asp Phe Val Gln Trp Leu Met Asn Thr Gly Gly Pro
            20                  25                  30

Ser Ser Gly Ala Pro Pro Pro Ser
        35                  40

<210> SEQ ID NO 2
<211> LENGTH: 40
<212> TYPE: PRT
<213> ORGANISM: Artificial
<220> FEATURE:
<223> OTHER INFORMATION: GLP-1R/GCGR Dual Target Agonist Polypeptide
<220> FEATURE:
<221> NAME/KEY: MISC_FEATURE
<222> LOCATION: (2)..(2)
<223> OTHER INFORMATION: D-Ser
<220> FEATURE:
<221> NAME/KEY: MISC_FEATURE
<222> LOCATION: (16)..(16)
<223> OTHER INFORMATION: X=Aib

<400> SEQUENCE: 2

His Ser Gln Gly Thr Phe Thr Ser Asp Tyr Ser Lys Lys Leu Asp Xaa
1               5                   10                  15

Arg Arg Ala Gln Asp Phe Val Gln Trp Leu Met Asn Thr Gly Gly Pro
            20                  25                  30

Ser Ser Gly Ala Pro Pro Pro Ser
        35                  40

<210> SEQ ID NO 3
<211> LENGTH: 40
<212> TYPE: PRT
```

```
<213> ORGANISM: Artificial
<220> FEATURE:
<223> OTHER INFORMATION: GLP-1R/GCGR Dual Target Agonist Polypeptide
<220> FEATURE:
<221> NAME/KEY: MISC_FEATURE
<222> LOCATION: (2)..(2)
<223> OTHER INFORMATION: D-Ser
<220> FEATURE:
<221> NAME/KEY: MISC_FEATURE
<222> LOCATION: (16)..(16)
<223> OTHER INFORMATION: X=Aib

<400> SEQUENCE: 3

His Ser Gln Gly Thr Phe Thr Ser Asp Tyr Ser Lys Lys Leu Asp Xaa
1               5                   10                  15

Arg Arg Ala Gln Asp Phe Val Gln Trp Leu Met Asn Thr Gly Gly Pro
            20                  25                  30

Ser Ser Gly Ala Pro Pro Pro Ser
        35                  40

<210> SEQ ID NO 4
<211> LENGTH: 40
<212> TYPE: PRT
<213> ORGANISM: Artificial
<220> FEATURE:
<223> OTHER INFORMATION: GLP-1R/GCGR Dual Target Agonist Polypeptide
<220> FEATURE:
<221> NAME/KEY: MISC_FEATURE
<222> LOCATION: (2)..(2)
<223> OTHER INFORMATION: D-Ser
<220> FEATURE:
<221> NAME/KEY: MISC_FEATURE
<222> LOCATION: (16)..(16)
<223> OTHER INFORMATION: X=Aib

<400> SEQUENCE: 4

His Ser Gln Gly Thr Phe Thr Ser Asp Lys Ser Lys Tyr Leu Asp Xaa
1               5                   10                  15

Arg Arg Ala Gln Asp Phe Val Gln Trp Leu Met Asn Thr Gly Gly Pro
            20                  25                  30

Ser Ser Gly Ala Pro Pro Pro Ser
        35                  40

<210> SEQ ID NO 5
<211> LENGTH: 40
<212> TYPE: PRT
<213> ORGANISM: Artificial
<220> FEATURE:
<223> OTHER INFORMATION: GLP-1R/GCGR Dual Target Agonist Polypeptide
<220> FEATURE:
<221> NAME/KEY: MISC_FEATURE
<222> LOCATION: (2)..(2)
<223> OTHER INFORMATION: D-Ser
<220> FEATURE:
<221> NAME/KEY: MISC_FEATURE
<222> LOCATION: (16)..(16)
<223> OTHER INFORMATION: X=Aib

<400> SEQUENCE: 5

His Ser Gln Gly Thr Phe Thr Ser Asp Lys Ser Lys Tyr Leu Asp Xaa
1               5                   10                  15

Arg Arg Ala Gln Asp Phe Val Gln Trp Leu Met Asn Thr Gly Gly Pro
            20                  25                  30

Ser Ser Gly Ala Pro Pro Pro Ser
        35                  40

<210> SEQ ID NO 6
```

```
<211> LENGTH: 40
<212> TYPE: PRT
<213> ORGANISM: Artificial
<220> FEATURE:
<223> OTHER INFORMATION: GLP-1R/GCGR Dual Target Agonist Polypeptide
<220> FEATURE:
<221> NAME/KEY: MISC_FEATURE
<222> LOCATION: (2)..(2)
<223> OTHER INFORMATION: D-Ser

<400> SEQUENCE: 6

His Ser Gln Gly Thr Phe Thr Ser Asp Tyr Ser Lys Tyr Leu Asp Lys
1               5                   10                  15

Arg Arg Ala Gln Asp Phe Val Gln Trp Leu Met Asn Thr Gly Gly Pro
            20                  25                  30

Ser Ser Gly Ala Pro Pro Pro Ser
        35                  40

<210> SEQ ID NO 7
<211> LENGTH: 40
<212> TYPE: PRT
<213> ORGANISM: Artificial
<220> FEATURE:
<223> OTHER INFORMATION: GLP-1R/GCGR Dual Target Agonist Polypeptide
<220> FEATURE:
<221> NAME/KEY: MISC_FEATURE
<222> LOCATION: (2)..(2)
<223> OTHER INFORMATION: D-Ser
<220> FEATURE:
<221> NAME/KEY: MISC_FEATURE
<222> LOCATION: (16)..(16)
<223> OTHER INFORMATION: X=Aib

<400> SEQUENCE: 7

His Ser Gln Gly Thr Phe Thr Ser Asp Tyr Ser Lys Tyr Leu Asp Xaa
1               5                   10                  15

Lys Arg Ala Gln Asp Phe Val Gln Trp Leu Met Asn Thr Gly Gly Pro
            20                  25                  30

Ser Ser Gly Ala Pro Pro Pro Ser
        35                  40

<210> SEQ ID NO 8
<211> LENGTH: 39
<212> TYPE: PRT
<213> ORGANISM: Artificial
<220> FEATURE:
<223> OTHER INFORMATION: GLP-1R/GCGR Dual Target Agonist Polypeptide
<220> FEATURE:
<221> NAME/KEY: MISC_FEATURE
<222> LOCATION: (2)..(2)
<223> OTHER INFORMATION: X=Aib
<220> FEATURE:
<221> NAME/KEY: MISC_FEATURE
<222> LOCATION: (16)..(16)
<223> OTHER INFORMATION: X=Aib

<400> SEQUENCE: 8

His Xaa Gln Gly Thr Phe Thr Ser Asp Lys Ser Lys Tyr Leu Asp Xaa
1               5                   10                  15

Arg Arg Ala Gln Asp Phe Val Gln Trp Leu Leu Asp Gly Gly Pro Ser
            20                  25                  30

Ser Gly Ala Pro Pro Pro Ser
        35

<210> SEQ ID NO 9
<211> LENGTH: 40
<212> TYPE: PRT
```

```
<213> ORGANISM: Artificial
<220> FEATURE:
<223> OTHER INFORMATION: GLP-1R/GCGR Dual Target Agonist Polypeptide
<220> FEATURE:
<221> NAME/KEY: MISC_FEATURE
<222> LOCATION: (2)..(2)
<223> OTHER INFORMATION: D-Ser
<220> FEATURE:
<221> NAME/KEY: MISC_FEATURE
<222> LOCATION: (16)..(16)
<223> OTHER INFORMATION: X=Aib

<400> SEQUENCE: 9

His Ser Gln Gly Thr Phe Thr Ser Asp Tyr Ser Lys Lys Leu Asp Xaa
1               5                   10                  15

Arg Arg Ala Gln Asp Phe Val Gln Trp Leu Met Asn Thr Gly Gly Pro
            20                  25                  30

Ser Ser Gly Ala Pro Pro Pro Ser
        35                  40

<210> SEQ ID NO 10
<211> LENGTH: 40
<212> TYPE: PRT
<213> ORGANISM: Artificial
<220> FEATURE:
<223> OTHER INFORMATION: GLP-1R/GCGR Dual Target Agonist Polypeptide
<220> FEATURE:
<221> NAME/KEY: MISC_FEATURE
<222> LOCATION: (2)..(2)
<223> OTHER INFORMATION: D-Ser
<220> FEATURE:
<221> NAME/KEY: MISC_FEATURE
<222> LOCATION: (16)..(16)
<223> OTHER INFORMATION: X=Aib

<400> SEQUENCE: 10

His Ser Gln Gly Thr Phe Thr Ser Asp Tyr Ser Lys Tyr Leu Asp Xaa
1               5                   10                  15

Lys Arg Ala Gln Asp Phe Val Gln Trp Leu Met Asn Thr Gly Gly Pro
            20                  25                  30

Ser Ser Gly Ala Pro Pro Pro Ser
        35                  40

<210> SEQ ID NO 11
<211> LENGTH: 39
<212> TYPE: PRT
<213> ORGANISM: Artificial
<220> FEATURE:
<223> OTHER INFORMATION: GLP-1R/GCGR Dual Target Agonist Polypeptide
<220> FEATURE:
<221> NAME/KEY: MISC_FEATURE
<222> LOCATION: (2)..(2)
<223> OTHER INFORMATION: X=Aib
<220> FEATURE:
<221> NAME/KEY: MISC_FEATURE
<222> LOCATION: (16)..(16)
<223> OTHER INFORMATION: X=Aib

<400> SEQUENCE: 11

His Xaa Gln Gly Thr Phe Thr Ser Asp Lys Ser Lys Tyr Leu Asp Xaa
1               5                   10                  15

Arg Arg Ala Gln Asp Phe Val Gln Trp Leu Leu Asp Gly Gly Pro Ser
            20                  25                  30

Ser Gly Ala Pro Pro Pro Ser
        35

<210> SEQ ID NO 12
```

```
<211> LENGTH: 39
<212> TYPE: PRT
<213> ORGANISM: Artificial
<220> FEATURE:
<223> OTHER INFORMATION: GLP-1R/GCGR Dual Target Agonist Polypeptide
<220> FEATURE:
<221> NAME/KEY: MISC_FEATURE
<222> LOCATION: (2)..(2)
<223> OTHER INFORMATION: X=Aib
<220> FEATURE:
<221> NAME/KEY: MISC_FEATURE
<222> LOCATION: (16)..(16)
<223> OTHER INFORMATION: X=Aib

<400> SEQUENCE: 12

His Xaa Gln Gly Thr Phe Thr Ser Asp Lys Ser Lys Tyr Leu Asp Xaa
1               5                   10                  15

Arg Arg Ala Gln Asp Phe Val Gln Trp Leu Leu Asp Gly Gly Pro Ser
            20                  25                  30

Ser Gly Ala Pro Pro Pro Ser
        35

<210> SEQ ID NO 13
<211> LENGTH: 39
<212> TYPE: PRT
<213> ORGANISM: Artificial
<220> FEATURE:
<223> OTHER INFORMATION: GLP-1R/GCGR Dual Target Agonist Polypeptide
<220> FEATURE:
<221> NAME/KEY: MISC_FEATURE
<222> LOCATION: (2)..(2)
<223> OTHER INFORMATION: X=Aib

<400> SEQUENCE: 13

His Xaa Gln Gly Thr Phe Thr Ser Asp Lys Ser Lys Tyr Leu Asp Glu
1               5                   10                  15

Arg Arg Ala Gln Asp Phe Val Gln Trp Leu Leu Asp Gly Gly Pro Ser
            20                  25                  30

Ser Gly Ala Pro Pro Pro Ser
        35

<210> SEQ ID NO 14
<211> LENGTH: 39
<212> TYPE: PRT
<213> ORGANISM: Artificial
<220> FEATURE:
<223> OTHER INFORMATION: GLP-1R/GCGR Dual Target Agonist Polypeptide
<220> FEATURE:
<221> NAME/KEY: MISC_FEATURE
<222> LOCATION: (2)..(2)
<223> OTHER INFORMATION: X=Aib

<400> SEQUENCE: 14

His Xaa Gln Gly Thr Phe Thr Ser Asp Lys Ser Lys Tyr Leu Asp Glu
1               5                   10                  15

Arg Arg Ala Gln Asp Phe Val Gln Trp Leu Leu Asp Gly Gly Pro Ser
            20                  25                  30

Ser Gly Ala Pro Pro Pro Ser
        35

<210> SEQ ID NO 15
<211> LENGTH: 39
<212> TYPE: PRT
<213> ORGANISM: Artificial
<220> FEATURE:
<223> OTHER INFORMATION: GLP-1R/GCGR Dual Target Agonist Polypeptide
<220> FEATURE:
```

```
<221> NAME/KEY: MISC_FEATURE
<222> LOCATION: (2)..(2)
<223> OTHER INFORMATION: X=Aib

<400> SEQUENCE: 15

His Xaa Gln Gly Thr Phe Thr Ser Asp Lys Ser Lys Tyr Leu Asp Glu
1               5                   10                  15

Arg Arg Ala Gln Asp Phe Val Gln Trp Leu Leu Asp Gly Gly Pro Ser
            20                  25                  30

Ser Gly Ala Pro Pro Pro Ser
        35

<210> SEQ ID NO 16
<211> LENGTH: 39
<212> TYPE: PRT
<213> ORGANISM: Artificial
<220> FEATURE:
<223> OTHER INFORMATION: GLP-1R/GCGR Dual Target Agonist Polypeptide
<220> FEATURE:
<221> NAME/KEY: MISC_FEATURE
<222> LOCATION: (2)..(2)
<223> OTHER INFORMATION: X=Aib

<400> SEQUENCE: 16

His Xaa Gln Gly Thr Phe Thr Ser Asp Lys Ser Lys Tyr Leu Asp Glu
1               5                   10                  15

Arg Arg Ala Gln Asp Phe Val Gln Trp Leu Leu Asp Gly Gly Pro Ser
            20                  25                  30

Ser Gly Ala Pro Pro Pro Ser
        35

<210> SEQ ID NO 17
<211> LENGTH: 29
<212> TYPE: PRT
<213> ORGANISM: Artificial
<220> FEATURE:
<223> OTHER INFORMATION: GLP-1R/GCGR Dual Target Agonist Polypeptide
<220> FEATURE:
<221> NAME/KEY: MISC_FEATURE
<222> LOCATION: (2)..(2)
<223> OTHER INFORMATION: D-Ser

<400> SEQUENCE: 17

His Ser Gln Gly Thr Phe Thr Ser Asp Tyr Ser Lys Tyr Leu Asp Ser
1               5                   10                  15

Lys Ala Ala His Asp Phe Val Glu Trp Leu Leu Arg Ala
            20                  25

<210> SEQ ID NO 18
<211> LENGTH: 29
<212> TYPE: PRT
<213> ORGANISM: Artificial
<220> FEATURE:
<223> OTHER INFORMATION: GLP-1R/GCGR Dual Target Agonist Polypeptide
<220> FEATURE:
<221> NAME/KEY: MISC_FEATURE
<222> LOCATION: (2)..(2)
<223> OTHER INFORMATION: D-Ser

<400> SEQUENCE: 18

His Ser Gln Gly Thr Phe Thr Ser Asp Tyr Ser Lys Tyr Leu Asp Glu
1               5                   10                  15

Lys Ala Ala Lys Glu Phe Ile Glu Trp Leu Leu Arg Ala
            20                  25
```

```
<210> SEQ ID NO 19
<211> LENGTH: 39
<212> TYPE: PRT
<213> ORGANISM: Artificial
<220> FEATURE:
<223> OTHER INFORMATION: GLP-1R/GCGR Dual Target Agonist Polypeptide
<220> FEATURE:
<221> NAME/KEY: MISC_FEATURE
<222> LOCATION: (2)..(2)
<223> OTHER INFORMATION: X=Aib
<220> FEATURE:
<221> NAME/KEY: MISC_FEATURE
<222> LOCATION: (16)..(16)
<223> OTHER INFORMATION: X=Aib

<400> SEQUENCE: 19

His Xaa Gln Gly Thr Phe Thr Ser Asp Lys Ser Lys Tyr Leu Asp Xaa
1               5                   10                  15

Arg Arg Ala Gln Asp Phe Val Gln Trp Leu Leu Asp Gly Gly Pro Ser
            20                  25                  30

Ser Gly Ala Pro Pro Pro Ser
        35

<210> SEQ ID NO 20
<211> LENGTH: 40
<212> TYPE: PRT
<213> ORGANISM: Artificial
<220> FEATURE:
<223> OTHER INFORMATION: GLP-1R/GCGR Dual Target Agonist Polypeptide
<220> FEATURE:
<221> NAME/KEY: MISC_FEATURE
<222> LOCATION: (2)..(2)
<223> OTHER INFORMATION: D-Ser
<220> FEATURE:
<221> NAME/KEY: MISC_FEATURE
<222> LOCATION: (16)..(16)
<223> OTHER INFORMATION: X=Aib

<400> SEQUENCE: 20

His Ser Gln Gly Thr Phe Thr Ser Asp Tyr Ser Lys Lys Leu Asp Xaa
1               5                   10                  15

Arg Arg Ala Gln Asp Phe Val Gln Trp Leu Met Asn Thr Gly Gly Pro
            20                  25                  30

Ser Ser Gly Ala Pro Pro Pro Ser
        35                  40

<210> SEQ ID NO 21
<211> LENGTH: 39
<212> TYPE: PRT
<213> ORGANISM: Artificial
<220> FEATURE:
<223> OTHER INFORMATION: GLP-1R/GCGR Dual Target Agonist Polypeptide
<220> FEATURE:
<221> NAME/KEY: MISC_FEATURE
<222> LOCATION: (2)..(2)
<223> OTHER INFORMATION: D-Ser

<400> SEQUENCE: 21

His Ser Gln Gly Thr Phe Thr Ser Asp Tyr Ser Lys Tyr Leu Asp Ser
1               5                   10                  15

Lys Ala Ala His Asp Phe Val Glu Trp Leu Leu Asn Gly Gly Pro Ser
            20                  25                  30

Ser Gly Ala Pro Pro Pro Ser
        35

<210> SEQ ID NO 22
<211> LENGTH: 39
```

```
<212> TYPE: PRT
<213> ORGANISM: Artificial
<220> FEATURE:
<223> OTHER INFORMATION: GLP-1R/GCGR Dual Target Agonist Polypeptide
<220> FEATURE:
<221> NAME/KEY: MISC_FEATURE
<222> LOCATION: (2)..(2)
<223> OTHER INFORMATION: D-Ser

<400> SEQUENCE: 22

His Ser Gln Gly Thr Phe Thr Ser Asp Tyr Ser Lys Tyr Leu Asp Ser
1               5                   10                  15

Lys Ala Ala His Asp Phe Val Glu Trp Leu Leu Asn Gly Gly Pro Ser
            20                  25                  30

Ser Gly Ala Pro Pro Pro Ser
            35

<210> SEQ ID NO 23
<211> LENGTH: 29
<212> TYPE: PRT
<213> ORGANISM: Artificial
<220> FEATURE:
<223> OTHER INFORMATION: GLP-1R/GCGR Dual Target Agonist Polypeptide
<220> FEATURE:
<221> NAME/KEY: MISC_FEATURE
<222> LOCATION: (2)..(2)
<223> OTHER INFORMATION: D-Ser

<400> SEQUENCE: 23

His Ser Gln Gly Thr Phe Thr Ser Asp Tyr Ser Lys Tyr Leu Asp Glu
1               5                   10                  15

Lys Ala Ala Lys Glu Phe Ile Glu Trp Leu Leu Arg Ala
            20                  25

<210> SEQ ID NO 24
<211> LENGTH: 29
<212> TYPE: PRT
<213> ORGANISM: Artificial
<220> FEATURE:
<223> OTHER INFORMATION: GLP-1R/GCGR Dual Target Agonist Polypeptide
<220> FEATURE:
<221> NAME/KEY: MISC_FEATURE
<222> LOCATION: (2)..(2)
<223> OTHER INFORMATION: D-Ser

<400> SEQUENCE: 24

His Ser Gln Gly Thr Phe Thr Ser Asp Tyr Ser Lys Tyr Leu Asp Glu
1               5                   10                  15

Lys Ala Ala Lys Glu Phe Ile Glu Trp Leu Leu Arg Ala
            20                  25

<210> SEQ ID NO 25
<211> LENGTH: 29
<212> TYPE: PRT
<213> ORGANISM: Artificial
<220> FEATURE:
<223> OTHER INFORMATION: GLP-1R/GCGR Dual Target Agonist Polypeptide
<220> FEATURE:
<221> NAME/KEY: MISC_FEATURE
<222> LOCATION: (2)..(2)
<223> OTHER INFORMATION: D-Ser

<400> SEQUENCE: 25

His Ser Gln Gly Thr Phe Thr Ser Asp Tyr Ser Lys Tyr Leu Asp Ser
1               5                   10                  15

Lys Ala Ala His Asp Phe Val Glu Trp Leu Leu Arg Ala
            20                  25
```

```
<210> SEQ ID NO 26
<211> LENGTH: 39
<212> TYPE: PRT
<213> ORGANISM: Artificial
<220> FEATURE:
<223> OTHER INFORMATION: GLP-1R/GCGR Dual Target Agonist Polypeptide
<220> FEATURE:
<221> NAME/KEY: MISC_FEATURE
<222> LOCATION: (2)..(2)
<223> OTHER INFORMATION: D-Ser

<400> SEQUENCE: 26

His Ser Gln Gly Thr Phe Thr Ser Asp Tyr Ser Lys Tyr Leu Asp Glu
1               5                   10                  15

Lys Ala Ala Lys Glu Phe Ile Glu Trp Leu Leu Asn Gly Gly Pro Ser
            20                  25                  30

Ser Gly Ala Pro Pro Pro Ser
        35

<210> SEQ ID NO 27
<211> LENGTH: 39
<212> TYPE: PRT
<213> ORGANISM: Artificial
<220> FEATURE:
<223> OTHER INFORMATION: GLP-1R/GCGR Dual Target Agonist Polypeptide
<220> FEATURE:
<221> NAME/KEY: MISC_FEATURE
<222> LOCATION: (2)..(2)
<223> OTHER INFORMATION: D-Ser

<400> SEQUENCE: 27

His Ser Gln Gly Thr Phe Thr Ser Asp Tyr Ser Lys Tyr Leu Asp Glu
1               5                   10                  15

Lys Ala Ala Lys Glu Phe Ile Glu Trp Leu Leu Asn Gly Gly Pro Ser
            20                  25                  30

Ser Gly Ala Pro Pro Pro Ser
        35

<210> SEQ ID NO 28
<211> LENGTH: 39
<212> TYPE: PRT
<213> ORGANISM: Artificial
<220> FEATURE:
<223> OTHER INFORMATION: GLP-1R/GCGR Dual Target Agonist Polypeptide
<220> FEATURE:
<221> NAME/KEY: MISC_FEATURE
<222> LOCATION: (2)..(2)
<223> OTHER INFORMATION: D-Ser

<400> SEQUENCE: 28

His Ser Gln Gly Thr Phe Thr Ser Asp Tyr Ser Lys Tyr Leu Asp Glu
1               5                   10                  15

Lys Ala Ala Lys Glu Phe Ile Glu Trp Leu Leu Asn Gly Gly Pro Ser
            20                  25                  30

Ser Gly Ala Pro Pro Pro Ser
        35

<210> SEQ ID NO 29
<211> LENGTH: 39
<212> TYPE: PRT
<213> ORGANISM: Artificial
<220> FEATURE:
<223> OTHER INFORMATION: GLP-1R/GCGR Dual Target Agonist Polypeptide
<220> FEATURE:
<221> NAME/KEY: MISC_FEATURE
```

<222> LOCATION: (2)..(2)
<223> OTHER INFORMATION: D-Ser

<400> SEQUENCE: 29

His Ser Gln Gly Thr Phe Thr Ser Asp Tyr Ser Lys Tyr Leu Asp Glu
1               5                   10                  15

Lys Ala Ala Lys Glu Phe Ile Glu Trp Leu Leu Asn Gly Gly Pro Ser
            20                  25                  30

Ser Gly Ala Pro Pro Ser
        35

<210> SEQ ID NO 30
<211> LENGTH: 40
<212> TYPE: PRT
<213> ORGANISM: Artificial
<220> FEATURE:
<223> OTHER INFORMATION: GLP-1R/GCGR Dual Target Agonist Polypeptide
<220> FEATURE:
<221> NAME/KEY: MISC_FEATURE
<222> LOCATION: (2)..(2)
<223> OTHER INFORMATION: D-Ser
<220> FEATURE:
<221> NAME/KEY: MISC_FEATURE
<222> LOCATION: (16)..(16)
<223> OTHER INFORMATION: X=Aib

<400> SEQUENCE: 30

His Ser Gln Gly Thr Phe Thr Ser Asp Lys Ser Lys Tyr Leu Asp Xaa
1               5                   10                  15

Arg Arg Ala Gln Asp Phe Val Gln Trp Leu Met Asn Thr Gly Gly Pro
            20                  25                  30

Ser Ser Gly Ala Pro Pro Ser
        35                  40

<210> SEQ ID NO 31
<211> LENGTH: 40
<212> TYPE: PRT
<213> ORGANISM: Artificial
<220> FEATURE:
<223> OTHER INFORMATION: GLP-1R/GCGR Dual Target Agonist Polypeptide
<220> FEATURE:
<221> NAME/KEY: MISC_FEATURE
<222> LOCATION: (2)..(2)
<223> OTHER INFORMATION: D-Ser
<220> FEATURE:
<221> NAME/KEY: MISC_FEATURE
<222> LOCATION: (16)..(16)
<223> OTHER INFORMATION: X=Aib

<400> SEQUENCE: 31

His Ser Gln Gly Thr Phe Thr Ser Asp Lys Ser Lys Tyr Leu Asp Xaa
1               5                   10                  15

Arg Arg Ala Gln Asp Phe Val Gln Trp Leu Met Asn Thr Gly Gly Pro
            20                  25                  30

Ser Ser Gly Ala Pro Pro Ser
        35                  40

<210> SEQ ID NO 32
<211> LENGTH: 40
<212> TYPE: PRT
<213> ORGANISM: Artificial
<220> FEATURE:
<223> OTHER INFORMATION: GLP-1R/GCGR Dual Target Agonist Polypeptide
<220> FEATURE:
<221> NAME/KEY: MISC_FEATURE
<222> LOCATION: (2)..(2)
<223> OTHER INFORMATION: D-Ser

```
<220> FEATURE:
<221> NAME/KEY: MISC_FEATURE
<222> LOCATION: (16)..(16)
<223> OTHER INFORMATION: X=Aib

<400> SEQUENCE: 32

His Ser Gln Gly Thr Phe Thr Ser Asp Lys Ser Lys Tyr Leu Asp Xaa
1               5                   10                  15

Arg Arg Ala Gln Asp Phe Val Gln Trp Leu Met Asn Thr Gly Gly Pro
            20                  25                  30

Ser Ser Gly Ala Pro Pro Pro Ser
        35                  40

<210> SEQ ID NO 33
<211> LENGTH: 40
<212> TYPE: PRT
<213> ORGANISM: Artificial
<220> FEATURE:
<223> OTHER INFORMATION: GLP-1R/GCGR Dual Target Agonist Polypeptide
<220> FEATURE:
<221> NAME/KEY: MISC_FEATURE
<222> LOCATION: (2)..(2)
<223> OTHER INFORMATION: D-Ser
<220> FEATURE:
<221> NAME/KEY: MISC_FEATURE
<222> LOCATION: (16)..(16)
<223> OTHER INFORMATION: X=Aib

<400> SEQUENCE: 33

His Ser Gln Gly Thr Phe Thr Ser Asp Tyr Ser Lys Tyr Leu Asp Xaa
1               5                   10                  15

Lys Arg Ala Gln Asp Phe Val Gln Trp Leu Met Asn Thr Gly Gly Pro
            20                  25                  30

Ser Ser Gly Ala Pro Pro Pro Ser
        35                  40

<210> SEQ ID NO 34
<211> LENGTH: 40
<212> TYPE: PRT
<213> ORGANISM: Artificial
<220> FEATURE:
<223> OTHER INFORMATION: GLP-1R/GCGR Dual Target Agonist Polypeptide
<220> FEATURE:
<221> NAME/KEY: MISC_FEATURE
<222> LOCATION: (2)..(2)
<223> OTHER INFORMATION: D-Ser

<400> SEQUENCE: 34

His Ser Gln Gly Thr Phe Thr Ser Asp Tyr Ser Lys Tyr Leu Asp Lys
1               5                   10                  15

Arg Arg Ala Gln Asp Phe Val Gln Trp Leu Met Asn Thr Gly Gly Pro
            20                  25                  30

Ser Ser Gly Ala Pro Pro Pro Ser
        35                  40

<210> SEQ ID NO 35
<211> LENGTH: 40
<212> TYPE: PRT
<213> ORGANISM: Artificial
<220> FEATURE:
<223> OTHER INFORMATION: GLP-1R/GCGR Dual Target Agonist Polypeptide
<220> FEATURE:
<221> NAME/KEY: MISC_FEATURE
<222> LOCATION: (2)..(2)
<223> OTHER INFORMATION: D-Ser

<400> SEQUENCE: 35
```

```
His Ser Gln Gly Thr Phe Thr Ser Asp Tyr Ser Lys Tyr Leu Asp Lys
1               5                   10                  15

Arg Arg Ala Gln Asp Phe Val Gln Trp Leu Met Asn Thr Gly Gly Pro
            20                  25                  30

Ser Ser Gly Ala Pro Pro Pro Ser
        35                  40

<210> SEQ ID NO 36
<211> LENGTH: 40
<212> TYPE: PRT
<213> ORGANISM: Artificial
<220> FEATURE:
<223> OTHER INFORMATION: GLP-1R/GCGR Dual Target Agonist Polypeptide
<220> FEATURE:
<221> NAME/KEY: MISC_FEATURE
<222> LOCATION: (2)..(2)
<223> OTHER INFORMATION: D-Ser

<400> SEQUENCE: 36

His Ser Gln Gly Thr Phe Thr Ser Asp Tyr Ser Lys Tyr Leu Asp Lys
1               5                   10                  15

Arg Arg Ala Gln Asp Phe Val Gln Trp Leu Met Asn Thr Gly Gly Pro
            20                  25                  30

Ser Ser Gly Ala Pro Pro Pro Ser
        35                  40

<210> SEQ ID NO 37
<211> LENGTH: 40
<212> TYPE: PRT
<213> ORGANISM: Artificial
<220> FEATURE:
<223> OTHER INFORMATION: GLP-1R/GCGR Dual Target Agonist Polypeptide
<220> FEATURE:
<221> NAME/KEY: MISC_FEATURE
<222> LOCATION: (2)..(2)
<223> OTHER INFORMATION: D-Ser
<220> FEATURE:
<221> NAME/KEY: MISC_FEATURE
<222> LOCATION: (27)..(27)
<223> OTHER INFORMATION: X=Nle

<400> SEQUENCE: 37

His Ser Gln Gly Thr Phe Thr Ser Asp Tyr Ser Lys Tyr Leu Asp Lys
1               5                   10                  15

Arg Arg Ala Gln Asp Phe Val Gln Trp Leu Xaa Asn Thr Gly Gly Pro
            20                  25                  30

Ser Ser Gly Ala Pro Pro Pro Ser
        35                  40

<210> SEQ ID NO 38
<211> LENGTH: 40
<212> TYPE: PRT
<213> ORGANISM: Artificial
<220> FEATURE:
<223> OTHER INFORMATION: GLP-1R/GCGR Dual Target Agonist Polypeptide
<220> FEATURE:
<221> NAME/KEY: MISC_FEATURE
<222> LOCATION: (2)..(2)
<223> OTHER INFORMATION: X=Aib, Ser or D-Ser
<220> FEATURE:
<221> NAME/KEY: MISC_FEATURE
<222> LOCATION: (10)..(10)
<223> OTHER INFORMATION: X=Lys or Tyr
<220> FEATURE:
<221> NAME/KEY: MISC_FEATURE
<222> LOCATION: (13)..(13)
<223> OTHER INFORMATION: X=Lys or Tyr
```

```
<220> FEATURE:
<221> NAME/KEY: MISC_FEATURE
<222> LOCATION: (16)..(16)
<223> OTHER INFORMATION: X=Ser, Aib, Lys or Glu
<220> FEATURE:
<221> NAME/KEY: MISC_FEATURE
<222> LOCATION: (17)..(17)
<223> OTHER INFORMATION: X=Lys or Arg
<220> FEATURE:
<221> NAME/KEY: MISC_FEATURE
<222> LOCATION: (18)..(18)
<223> OTHER INFORMATION: Arg or Ala
<220> FEATURE:
<221> NAME/KEY: MISC_FEATURE
<222> LOCATION: (20)..(20)
<223> OTHER INFORMATION: X=His, Gln or Lys
<220> FEATURE:
<221> NAME/KEY: MISC_FEATURE
<222> LOCATION: (21)..(21)
<223> OTHER INFORMATION: X=Asp or Glu
<220> FEATURE:
<221> NAME/KEY: MISC_FEATURE
<222> LOCATION: (23)..(23)
<223> OTHER INFORMATION: X=Ile, Leu or Val
<220> FEATURE:
<221> NAME/KEY: MISC_FEATURE
<222> LOCATION: (24)..(24)
<223> OTHER INFORMATION: X=Glu or Gln
<220> FEATURE:
<221> NAME/KEY: MISC_FEATURE
<222> LOCATION: (27)..(27)
<223> OTHER INFORMATION: X=Met, Leu, Nle or is absent
<220> FEATURE:
<221> NAME/KEY: MISC_FEATURE
<222> LOCATION: (28)..(28)
<223> OTHER INFORMATION: X=Ser, Asp, Asn, Arg or is absent
<220> FEATURE:
<221> NAME/KEY: MISC_FEATURE
<222> LOCATION: (29)..(29)
<223> OTHER INFORMATION: X=Ala, Gly, Thr or is absent
<220> FEATURE:
<221> NAME/KEY: MISC_FEATURE
<222> LOCATION: (30)..(30)
<223> OTHER INFORMATION: X=Gly or is absent
<220> FEATURE:
<221> NAME/KEY: MISC_FEATURE
<222> LOCATION: (31)..(31)
<223> OTHER INFORMATION: X=Gly or is absent
<220> FEATURE:
<221> NAME/KEY: MISC_FEATURE
<222> LOCATION: (32)..(32)
<223> OTHER INFORMATION: X=Pro or is absent
<220> FEATURE:
<221> NAME/KEY: MISC_FEATURE
<222> LOCATION: (33)..(33)
<223> OTHER INFORMATION: X=Ser or is absent
<220> FEATURE:
<221> NAME/KEY: MISC_FEATURE
<222> LOCATION: (34)..(34)
<223> OTHER INFORMATION: X=Ser or is absent
<220> FEATURE:
<221> NAME/KEY: MISC_FEATURE
<222> LOCATION: (35)..(35)
<223> OTHER INFORMATION: X=Gly or is absent
<220> FEATURE:
<221> NAME/KEY: MISC_FEATURE
<222> LOCATION: (36)..(36)
<223> OTHER INFORMATION: X=Ala or is absent
<220> FEATURE:
<221> NAME/KEY: MISC_FEATURE
<222> LOCATION: (37)..(37)
<223> OTHER INFORMATION: X=Pro or is absent
<220> FEATURE:
<221> NAME/KEY: MISC_FEATURE
<222> LOCATION: (38)..(38)
<223> OTHER INFORMATION: X=Pro or is absent
<220> FEATURE:
<221> NAME/KEY: MISC_FEATURE
<222> LOCATION: (39)..(39)
```

```
<223> OTHER INFORMATION: X=Pro or is absent
<220> FEATURE:
<221> NAME/KEY: MISC_FEATURE
<222> LOCATION: (40)..(40)
<223> OTHER INFORMATION: X=Ser or is absent

<400> SEQUENCE: 38

His Xaa Gln Gly Thr Phe Thr Ser Asp Xaa Ser Lys Xaa Leu Asp Xaa
1               5                   10                  15

Xaa Xaa Ala Xaa Xaa Phe Xaa Xaa Trp Leu Xaa Xaa Xaa Xaa Xaa Xaa
            20              25                  30

Xaa Xaa Xaa Xaa Xaa Xaa Xaa Xaa
        35                  40
```